United States Patent
Mori et al.

(10) Patent No.: US 11,505,789 B2
(45) Date of Patent: Nov. 22, 2022

(54) ENZYME EXHIBITING ALPHA-1,6-GLUCOSYL TRANSFER ACTIVITY

(71) Applicants: National University Corporation Hokkaido University, Sapporo (JP); Nihon Shokuhin Kako Co., Ltd., Tokyo (JP)

(72) Inventors: Haruhide Mori, Sapporo (JP); Wataru Saburi, Sapporo (JP); Kenta Kanai, Fuji (JP); Kenta Aizawa, Fuji (JP); Takahisa Iizuka, Fuji (JP); Noriaki Takechi, Fuji (JP); Mioka Tani, Fuji (JP)

(73) Assignees: National University Corporation Hokkaido University; Nihon Shokuhin Kako Co., Ltd.

( * ) Notice: Subject to any disclaimer, the term of this patent is extended or adjusted under 35 U.S.C. 154(b) by 7 days.

(21) Appl. No.: 16/971,169

(22) PCT Filed: Feb. 19, 2019

(86) PCT No.: PCT/JP2019/006111
§ 371 (c)(1),
(2) Date: Aug. 19, 2020

(87) PCT Pub. No.: WO2019/163777
PCT Pub. Date: Aug. 29, 2019

(65) Prior Publication Data
US 2021/0009977 A1    Jan. 14, 2021

(30) Foreign Application Priority Data
Feb. 20, 2018  (JP) .............................. JP2018-028272

(51) Int. Cl.
*C12N 9/44* (2006.01)
*C12P 19/18* (2006.01)

(52) U.S. Cl.
CPC ............ *C12N 9/2451* (2013.01); *C12P 19/18* (2013.01); *C12Y 302/01033* (2013.01)

(58) Field of Classification Search
CPC ........ A23V 2002/00; A23V 2250/5034; C12P 19/18; C12P 19/04; A23K 20/163; A61K 2800/86; A61K 8/732; A61K 31/716; A61K 2800/101; A61K 8/73; C12N 9/2451; C12N 9/10; A23L 33/20; A61Q 19/00; C08B 37/00; C12Y 302/01033
See application file for complete search history.

(56) References Cited

U.S. PATENT DOCUMENTS
2017/0304353 A1   10/2017 Aizawa et al.

FOREIGN PATENT DOCUMENTS

| JP | H08173178 A | 7/1996 |
|---|---|---|
| JP | 2001258589 A | 9/2001 |
| JP | 2007181452 A | 7/2007 |
| JP | 201295606 A | 5/2012 |
| JP | 2015205856 A | 11/2015 |
| JP | 2017114943 A | 6/2017 |
| WO | 2016047616 A1 | 3/2016 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Glycosyl hydrolase, glucoamylase [Thermoanaerobactersiderophilus SR4], GenBank: EIV99888.1, Mar. 18, 2015, 3 pages. (Year: 2015).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Coutinho, "Glycoside Hydrolase Family 15", Retrieved from http://www.cazypedia.org/index.php?title=Glycoside_Hydrolase_Family_15&oldid=6695, cited on May 9, 2011.
Ichinose et al., *Paenibacillus* sp. 598K 6-α-glucosyltransferase is essential for cycloisomaltooligosaccharide synthesis from α-(1 -> 4)-glucan, Appl Microbiol Biotechnol, 2017, vol. 101, p. 4115-4128.

(Continued)

*Primary Examiner* — Ganapathirama Raghu
(74) *Attorney, Agent, or Firm* — The Webb Law Firm

(57) ABSTRACT

The present invention relates to an enzyme having α-1,6-glucosyl transfer activity, which can use a partially degraded starch product as a substrate and is heat resistant and suitable for industrial applications; an enzyme preparation for use in manufacturing α-1,6-glucan, comprising the enzyme as an active ingredient; and a method for manufacturing α-1,6-glucan using the enzyme or enzyme preparation. The present invention provides an enzyme having α-1,6-glucosyl transfer activity, which is any one of proteins (a), (b), and (c): (a) a protein consisting of an amino acid sequence of SEQ ID NO: 3; (b) a protein consisting of an amino acid sequence having at least 90% amino acid sequence identity to the amino acid sequence of SEQ ID NO: 3; and (c) a protein consisting of an amino acid sequence in which one or several amino acid(s) have been substituted, inserted, deleted and/or added in the amino acid sequence of SEQ ID NO: 3.

15 Claims, 11 Drawing Sheets
Specification includes a Sequence Listing.

(56) References Cited

OTHER PUBLICATIONS

Mishima et al., "Analysis of the transglycosylation exhibited by the GH15 domain-containing enzyme that is derived from Thermoanaerobacter Siderophilus", Journal of Applied Glycoscience, 2017, vol. 7:3, p. 1-3, Abstract.

NCBI SARS-Cov-2 literature, sequence, and clinical content: https://www.ncbi.nlmnih.gov/sars-cov-2/, GenBank: EIV998880.1, glycosyl hydrolase, glucoamylase [Thermoanaerobacter siderophilus SR4], p. 1-2.

Slobodkin et al., "*Thermoanaerobacter siderophilus* sp nov., a novel dissimilatory FE(III)-reducing, anaerobic, thermophilic bacterium", International Journal of Systematic Bacteriology, 1999, vol. 49, p. 1471-1478.

Suzuki et al., "Simple Purification and Characterization of an Extracellular Dextrin Dextranase from Acetobacter capsulatum ATCC 11894", J Appl. Clycosci, 1999, vol. 46:4, p. 469-473.

"Thermoanaerobacter siderophilus GH-15", The Japanese Society of Applied Glycoscience, Annual Meeting in 2017 (66th), Sep. 7, 2017, Applied Glycoscience Symposium, Nihon University, College of Bioresource Sciences, Shonan Campus, p. 1-7.

\* cited by examiner

```
MLSLYRRKLFITILIVIFVLSNFFTLFTYPISPGVSVAYAASTGNLIQRV
YTDKARYNPGDLVTISADLINKTGSTWSGTLTLQINKLESQIYTASQSVT
LANGDSTTITFTWTAPPTDFVGYYAGIAAGSTDFNGTGIDVSSSPLRFPR
YGFISNFPVSQTVQQSTDMVKQMVEDYHLNLFQFYDWMWRHEKLIKRTNG
VIDSTWVDLFDRTLSWQTIQNNVAAVHSFNAYAMAYAMSYAAREGYEQMW
GISPTWGIFQDTAHQSQFNVDFHNGKFLWLFNPANVNWQSWIISEYKDAI
NTAGFDGIQIDQMGQRDNVYDYTGFSVTLPSTFAQFLQQVKSELESNNAK
KNVVTFNIVDGTVNGWAAGEIARYGASDFDFSEIWWKANTYNDLRNYIEW
LRQNNGGKPVVLAAYMNYNQEYGPIYEAESAILSGVSVNTNHPGYTGTGF
VDGFETVGDSITWTIDFPETGDYSFVFRYANATGATATRNVYVDGRLLGQ
VSFANQVNWDTWVADAWIQIEGLTAGTHSVTLKYDSDNIGAINVDHLTLG
EFEEHSVRLADAMMFASGATHIELGDTNQMLAHEYYPNRSKSMRNSLKAA
MRDYYSFATAYENLLFDPNIVPADQGNQWIALTTGQPLSGNGTSGTIWQM
VKRKSDYDIIHLINLMGNDDQWRNPAVQPTFQSNIGVKYYPGPNAAVSGV
YLASPDLHGMTIPLIYTTGNDSRGNYIQFTVPSLKYWDMIYVKRTITTP
PDGQYEAEYAIKSGTNINTDHTGYTGSGFVDNFDASGKGVSFIINVPTSD
IYTLRFRYGNGGTTIATRNLFIDGQYAGTLQFRNLYNWDVWDTVETTVWL
SAGVHQVVLWYSPENDGAINLDNLIVLQQTTSARTSARSFWMNNWSNLIG
IHMASKLSPTDNGNYGPRLAELHFRGDWPTNQIVDATAFFRDETDLTPIK
YTNAHSFDSEAWFENDGTLTVRYLNYNGSALPVQITKQYAMVPNQNFLVI
KYTFLNQTSNARTLNFLEQVHLNNKTSSDPNPGWQHGWWDVSRNALGTDM
SQTGQFYIELGAFQTMDSYQVGNDADSNPNSQTSSPWYQFDANGVLNRCG
DLWSQNLSMGFQKLITVPAGGSVTLAFYYAIGSTQEEAEAAADLARSQTA
DYWFTQTAAEYNNWLNSGQRVNTSDIGINTAFDRSLIINKQAQHPEFGSW
PAATNPSYQYKVWVRDSAVTAMGMDAANHLSEAEKYWNWMASVQNTDGTW
HTNYNVWKANEWISFVEPEHDAIGLFLIGVYQHYSLLKSRDPSAATTFLN
NIWTQVTRAGDFIYKNIGASGFGPADASIWEEQVEYNIFTQVTYAAGLNA
GRLLAQEKGDITRANNYLSGAQIIKDAILRSFLSSPRGLWNESNRYFNRA
INTDGTARTTVDASSDLIWVFGLLSPTDTRIRDHRIKVLSRLTHDRYGIA
RYENDEFYYSSPYSPGGQYEAGAAEPVWPQMTMYASMIEHWRGDDATALA
RLKWYVSRTARGYVTPGEAVDWTNGQPLISTAVEPVTGSWFQMAVLTYSN
QFDPRLPDF
```

Predicted domain structure (170kDa)

SEQUENCE LISTING

```
<160> NUMBER OF SEQ ID NOS: 12

<210> SEQ ID NO 1
<211> LENGTH: 1559
<212> TYPE: PRT
<213> ORGANISM: Thermoanaerobacter siderophilus

<400> SEQUENCE: 1

Met Leu Ser Leu Tyr Arg Arg Lys Leu Phe Ile Thr Ile Leu Ile Val
1               5                   10                  15

Ile Phe Val Leu Ser Asn Phe Phe Thr Leu Phe Thr Tyr Pro Ile Ser
            20                  25                  30

Pro Gly Val Ser Val Ala Tyr Ala Ala Ser Thr Gly Asn Leu Ile Gln
        35                  40                  45

Arg Val Tyr Thr Asp Lys Ala Arg Tyr Asn Pro Gly Asp Leu Val Thr
    50                  55                  60

Ile Ser Ala Asp Leu Ile Asn Lys Thr Gly Ser Thr Trp Ser Gly Thr
65                  70                  75                  80

Leu Thr Leu Gln Ile Asn Lys Leu Glu Ser Gln Ile Tyr Thr Ala Ser
                85                  90                  95

Gln Ser Val Thr Leu Ala Asn Gly Asp Ser Thr Thr Ile Thr Phe Thr
            100                 105                 110

Trp Thr Ala Pro Pro Thr Asp Phe Val Gly Tyr Tyr Ala Gly Ile Ala
        115                 120                 125

Ala Gly Ser Thr Asp Phe Asn Gly Thr Gly Ile Asp Val Ser Ser Ser
    130                 135                 140

Pro Leu Arg Phe Pro Arg Tyr Gly Phe Ile Ser Asn Phe Pro Val Ser
145                 150                 155                 160

Gln Thr Val Gln Gln Ser Thr Asp Met Val Lys Gln Met Val Glu Asp
                165                 170                 175

Tyr His Leu Asn Leu Phe Gln Phe Tyr Asp Trp Met Trp Arg His Glu
            180                 185                 190

Lys Leu Ile Lys Arg Thr Asn Gly Val Ile Asp Ser Thr Trp Val Asp
        195                 200                 205

Leu Phe Asp Arg Thr Leu Ser Trp Gln Thr Ile Gln Asn Asn Val Ala
    210                 215                 220

Ala Val His Ser Phe Asn Ala Tyr Ala Met Ala Tyr Ala Met Ser Tyr
225                 230                 235                 240

Ala Ala Arg Glu Gly Tyr Glu Gln Met Trp Gly Ile Ser Pro Thr Trp
                245                 250                 255

Gly Ile Phe Gln Asp Thr Ala His Gln Ser Gln Phe Asn Val Asp Phe
            260                 265                 270

His Asn Gly Lys Phe Leu Trp Leu Phe Asn Pro Ala Asn Val Asn Trp
        275                 280                 285

Gln Ser Trp Ile Ile Ser Glu Tyr Lys Asp Ala Ile Asn Thr Ala Gly
    290                 295                 300

Phe Asp Gly Ile Gln Ile Asp Gln Met Gly Gln Arg Asp Asn Val Tyr
```

```
         305                 310                 315                 320
Asp Tyr Thr Gly Phe Ser Val Thr Leu Pro Ser Thr Phe Ala Gln Phe
                    325                 330                 335
Leu Gln Gln Val Lys Ser Glu Leu Glu Ser Asn Asn Ala Lys Lys Asn
                    340                 345                 350
Val Val Thr Phe Asn Ile Val Asp Gly Thr Val Asn Gly Trp Ala Ala
                    355                 360                 365
Gly Glu Ile Ala Arg Tyr Gly Ala Ser Asp Phe Asp Phe Ser Glu Ile
                    370                 375                 380
Trp Trp Lys Ala Asn Thr Tyr Asn Asp Leu Arg Asn Tyr Ile Glu Trp
385                 390                 395                 400
Leu Arg Gln Asn Asn Gly Gly Lys Pro Val Val Leu Ala Ala Tyr Met
                    405                 410                 415
Asn Tyr Asn Gln Glu Tyr Gly Pro Ile Tyr Glu Ala Glu Ser Ala Ile
                    420                 425                 430
Leu Ser Gly Val Ser Val Asn Thr Asn His Pro Gly Tyr Thr Gly Thr
                    435                 440                 445
Gly Phe Val Asp Gly Phe Glu Thr Val Gly Asp Ser Ile Thr Trp Thr
                    450                 455                 460
Ile Asp Phe Pro Glu Thr Gly Asp Tyr Ser Phe Val Phe Arg Tyr Ala
465                 470                 475                 480
Asn Ala Thr Gly Ala Thr Ala Thr Arg Asn Val Tyr Val Asp Gly Arg
                    485                 490                 495
Leu Leu Gly Gln Val Ser Phe Ala Asn Gln Val Asn Trp Asp Thr Trp
                    500                 505                 510
Val Ala Asp Ala Trp Ile Gln Ile Glu Gly Leu Thr Ala Gly Thr His
                    515                 520                 525
Ser Val Thr Leu Lys Tyr Asp Ser Asp Asn Ile Gly Ala Ile Asn Val
                    530                 535                 540
Asp His Leu Thr Leu Gly Glu Phe Glu Glu His Ser Val Arg Leu Ala
545                 550                 555                 560
Asp Ala Met Met Phe Ala Ser Gly Ala Thr His Ile Glu Leu Gly Asp
                    565                 570                 575
Thr Asn Gln Met Leu Ala His Glu Tyr Tyr Pro Asn Arg Ser Lys Ser
                    580                 585                 590
Met Arg Asn Ser Leu Lys Ala Ala Met Arg Asp Tyr Tyr Ser Phe Ala
                    595                 600                 605
Thr Ala Tyr Glu Asn Leu Leu Phe Asp Pro Asn Ile Val Pro Ala Asp
                    610                 615                 620
Gln Gly Asn Gln Trp Ile Ala Leu Thr Thr Gly Gln Pro Leu Ser Gly
625                 630                 635                 640
Asn Gly Thr Ser Gly Thr Ile Trp Gln Met Val Lys Arg Lys Ser Asp
                    645                 650                 655
Tyr Asp Ile Ile His Leu Ile Asn Leu Met Gly Asn Asp Gln Trp
                    660                 665                 670
Arg Asn Pro Ala Val Gln Pro Thr Phe Gln Ser Asn Ile Gly Val Lys
                    675                 680                 685
Tyr Tyr Pro Gly Pro Asn Ala Ala Val Ser Gly Val Tyr Leu Ala Ser
                    690                 695                 700
Pro Asp Leu Asp His Gly Met Thr Ile Pro Leu Ile Tyr Thr Thr Gly
705                 710                 715                 720
Asn Asp Ser Arg Gly Asn Tyr Ile Gln Phe Thr Val Pro Ser Leu Lys
                    725                 730                 735
```

-continued

Tyr Trp Asp Met Ile Tyr Val Lys Arg Thr Ile Thr Pro Pro Asp
            740                 745                 750

Gly Gln Tyr Glu Ala Glu Tyr Ala Ile Lys Ser Gly Thr Asn Ile Asn
            755                 760                 765

Thr Asp His Thr Gly Tyr Thr Gly Ser Gly Phe Val Asp Asn Phe Asp
770                 775                 780

Ala Ser Gly Lys Gly Val Ser Phe Ile Ile Asn Val Pro Thr Ser Asp
785                 790                 795                 800

Thr Tyr Thr Leu Arg Phe Arg Tyr Gly Asn Gly Thr Thr Ile Ala
            805                 810                 815

Thr Arg Asn Leu Phe Ile Asp Gly Gln Tyr Ala Gly Thr Leu Gln Phe
            820                 825                 830

Arg Asn Leu Tyr Asn Trp Asp Val Trp Asp Thr Val Glu Thr Thr Val
            835                 840                 845

Trp Leu Ser Ala Gly Val His Gln Val Val Leu Trp Tyr Ser Pro Glu
            850                 855                 860

Asn Asp Gly Ala Ile Asn Leu Asp Asn Leu Ile Val Leu Gln Gln Thr
865                 870                 875                 880

Thr Ser Ala Arg Thr Ser Ala Arg Ser Phe Trp Met Asn Asn Trp Ser
            885                 890                 895

Asn Leu Ile Gly Ile His Met Ala Ser Lys Leu Ser Pro Thr Asp Asn
            900                 905                 910

Gly Asn Tyr Gly Pro Arg Leu Ala Glu Leu His Phe Arg Gly Asp Trp
            915                 920                 925

Pro Thr Asn Gln Ile Val Asp Ala Thr Ala Phe Phe Arg Asp Glu Thr
            930                 935                 940

Asp Leu Thr Pro Ile Lys Tyr Thr Asn Ala His Ser Phe Asp Ser Glu
945                 950                 955                 960

Ala Trp Phe Glu Asn Asp Gly Thr Leu Thr Val Arg Tyr Leu Asn Tyr
            965                 970                 975

Asn Gly Ser Ala Leu Pro Val Gln Ile Thr Lys Gln Tyr Ala Met Val
            980                 985                 990

Pro Asn Gln Asn Phe Leu Val Ile Lys Tyr Thr Phe Leu Asn Gln Thr
            995                 1000                1005

Ser Asn Ala Arg Thr Leu Asn Phe Leu Glu Gln Val His Leu Asn
            1010                1015                1020

Asn Lys Thr Ser Ser Asp Pro Asn Pro Gly Trp Gln His Gly Trp
            1025                1030                1035

Trp Asp Val Ser Arg Asn Ala Leu Gly Thr Asp Met Ser Gln Thr
            1040                1045                1050

Gly Gln Phe Tyr Ile Glu Leu Gly Ala Phe Gln Thr Met Asp Ser
            1055                1060                1065

Tyr Gln Val Gly Asn Asp Ala Asp Ser Asn Pro Asn Ser Gln Thr
            1070                1075                1080

Ser Ser Pro Trp Tyr Gln Phe Asp Ala Asn Gly Val Leu Asn Arg
            1085                1090                1095

Cys Gly Asp Leu Trp Ser Gln Asn Leu Ser Met Gly Phe Gln Lys
            1100                1105                1110

Leu Ile Thr Val Pro Ala Gly Gly Ser Val Thr Leu Ala Phe Tyr
            1115                1120                1125

Tyr Ala Ile Gly Ser Thr Gln Glu Glu Ala Glu Ala Ala Asp
            1130                1135                1140

-continued

| | | | | | | | | | | | |
|---|---|---|---|---|---|---|---|---|---|---|---|
| Leu | Ala | Arg | Ser | Gln | Thr | Ala | Asp | Tyr | Trp | Phe | Thr | Gln | Thr | Ala |
| | 1145 | | | | | 1150 | | | | | 1155 | | | |
| Ala | Glu | Tyr | Asn | Asn | Trp | Leu | Asn | Ser | Gly | Gln | Arg | Val | Asn | Thr |
| | 1160 | | | | | 1165 | | | | | 1170 | | | |
| Ser | Asp | Ile | Gly | Ile | Asn | Thr | Ala | Phe | Asp | Arg | Ser | Leu | Ile | Ile |
| | 1175 | | | | | 1180 | | | | | 1185 | | | |
| Asn | Lys | Gln | Ala | Gln | His | Pro | Glu | Phe | Gly | Ser | Trp | Pro | Ala | Ala |
| | 1190 | | | | | 1195 | | | | | 1200 | | | |
| Thr | Asn | Pro | Ser | Tyr | Gln | Tyr | Lys | Val | Trp | Val | Arg | Asp | Ser | Ala |
| | 1205 | | | | | 1210 | | | | | 1215 | | | |
| Val | Thr | Ala | Met | Gly | Met | Asp | Ala | Ala | Asn | His | Leu | Ser | Glu | Ala |
| | 1220 | | | | | 1225 | | | | | 1230 | | | |
| Glu | Lys | Tyr | Trp | Asn | Trp | Met | Ala | Ser | Val | Gln | Asn | Thr | Asp | Gly |
| | 1235 | | | | | 1240 | | | | | 1245 | | | |
| Thr | Trp | His | Thr | Asn | Tyr | Asn | Val | Trp | Lys | Ala | Asn | Glu | Trp | Ile |
| | 1250 | | | | | 1255 | | | | | 1260 | | | |
| Ser | Phe | Val | Glu | Pro | Glu | His | Asp | Ala | Ile | Gly | Leu | Phe | Leu | Ile |
| | 1265 | | | | | 1270 | | | | | 1275 | | | |
| Gly | Val | Tyr | Gln | His | Tyr | Ser | Leu | Leu | Lys | Ser | Arg | Asp | Pro | Ser |
| | 1280 | | | | | 1285 | | | | | 1290 | | | |
| Ala | Ala | Thr | Thr | Phe | Leu | Asn | Asn | Ile | Trp | Thr | Gln | Val | Thr | Arg |
| | 1295 | | | | | 1300 | | | | | 1305 | | | |
| Ala | Gly | Asp | Phe | Ile | Tyr | Lys | Asn | Ile | Gly | Ala | Ser | Gly | Phe | Gly |
| | 1310 | | | | | 1315 | | | | | 1320 | | | |
| Pro | Ala | Asp | Ala | Ser | Ile | Trp | Glu | Glu | Gln | Val | Glu | Tyr | Asn | Ile |
| | 1325 | | | | | 1330 | | | | | 1335 | | | |
| Phe | Thr | Gln | Val | Thr | Tyr | Ala | Ala | Gly | Leu | Asn | Ala | Gly | Arg | Leu |
| | 1340 | | | | | 1345 | | | | | 1350 | | | |
| Leu | Ala | Gln | Glu | Lys | Gly | Asp | Ile | Thr | Arg | Ala | Asn | Asn | Tyr | Leu |
| | 1355 | | | | | 1360 | | | | | 1365 | | | |
| Ser | Gly | Ala | Gln | Ile | Ile | Lys | Asp | Ala | Ile | Leu | Arg | Ser | Phe | Leu |
| | 1370 | | | | | 1375 | | | | | 1380 | | | |
| Ser | Ser | Pro | Arg | Gly | Leu | Trp | Asn | Glu | Ser | Asn | Arg | Tyr | Phe | Asn |
| | 1385 | | | | | 1390 | | | | | 1395 | | | |
| Arg | Ala | Ile | Asn | Thr | Asp | Gly | Thr | Ala | Arg | Thr | Thr | Val | Asp | Ala |
| | 1400 | | | | | 1405 | | | | | 1410 | | | |
| Ser | Ser | Asp | Leu | Ile | Trp | Val | Phe | Gly | Leu | Leu | Ser | Pro | Thr | Asp |
| | 1415 | | | | | 1420 | | | | | 1425 | | | |
| Thr | Arg | Ile | Arg | Asp | His | Arg | Ile | Lys | Val | Leu | Ser | Arg | Leu | Thr |
| | 1430 | | | | | 1435 | | | | | 1440 | | | |
| His | Asp | Arg | Tyr | Gly | Ile | Ala | Arg | Tyr | Glu | Asn | Asp | Glu | Phe | Tyr |
| | 1445 | | | | | 1450 | | | | | 1455 | | | |
| Tyr | Ser | Ser | Pro | Tyr | Ser | Pro | Gly | Gly | Gln | Tyr | Glu | Ala | Gly | Ala |
| | 1460 | | | | | 1465 | | | | | 1470 | | | |
| Ala | Glu | Pro | Val | Trp | Pro | Gln | Met | Thr | Met | Tyr | Ala | Ser | Met | Ile |
| | 1475 | | | | | 1480 | | | | | 1485 | | | |
| Glu | His | Trp | Arg | Gly | Asp | Asp | Ala | Thr | Ala | Leu | Ala | Arg | Leu | Lys |
| | 1490 | | | | | 1495 | | | | | 1500 | | | |
| Trp | Tyr | Val | Ser | Arg | Thr | Ala | Arg | Gly | Tyr | Val | Thr | Pro | Gly | Glu |
| | 1505 | | | | | 1510 | | | | | 1515 | | | |
| Ala | Val | Asp | Trp | Thr | Asn | Gly | Gln | Pro | Leu | Ile | Ser | Thr | Ala | Val |
| | 1520 | | | | | 1525 | | | | | 1530 | | | |
| Glu | Pro | Val | Thr | Gly | Ser | Trp | Phe | Gln | Met | Ala | Val | Leu | Thr | Tyr |

Ser Asn Gln Phe Asp Pro Arg Leu Pro Asp Phe
    1550              1555

<210> SEQ ID NO 2
<211> LENGTH: 4680
<212> TYPE: DNA
<213> ORGANISM: Thermoanaerobacter siderophilus

<400> SEQUENCE: 2

| | | |
|---|---|---|
| atgctgagcc tgtaccgtcg taaactcttc atcaccattc tgattgtgat cttcgtcctg | 60 |
| tcgaacttct tcacgctgtt cacctatccg attagtcccg tgtgtctgt tgcgtatgcg | 120 |
| gcgtctacgg gtaatctcat ccagcgtgtc tacaccgata agcacggta taatccgggc | 180 |
| gatctcgtga ccatttccgc tgatcttatt aacaaaaccg gttccacctg gagcggcacc | 240 |
| ttaaccctcc aaattaacaa acttgagagc cagatctaca ctgcaagcca gtcagtaact | 300 |
| ctggccaacg gggatagcac aaccattaca tttacctgga cggctcctcc gacggatttt | 360 |
| gttggatact atgccggtat tgccgcagga agtacggatt taacggcac aggcattgat | 420 |
| gtttctagca gcccgttacg cttccgcgc tatggcttta tctcgaactt ccctgtgtcc | 480 |
| caaacggttc agcagtcaac cgacatggtg aaacagatgg tggaagatta tcaccttaac | 540 |
| ttatttcagt tctatgactg gatgtggcgc catgaaaagc tgatcaaacg cacaaacggc | 600 |
| gtcattgaca gcacctgggt cgatctgttc gatcgtactc tgagttggca gacgatccag | 660 |
| aacaacgtag ccgcggttca ttcgtttaac gcatacgcta tggcctatgc gatgtcttat | 720 |
| gcagcgcgtg agggctatga caaatgtggg gtatttcac caacgtgggg cattttccag | 780 |
| gataccgcgc atcaatctca gtttaacgtt gattttcaca cggcaaatt tctgtggctt | 840 |
| ttcaatccgg caaatgtgaa ttggcagtcc tggattattt cggagtataa agatgcgatc | 900 |
| aataccgcag gctttgatgg aatccaaatc gaccagatgg gtcaacgcga taatgtgtat | 960 |
| gattatacag gctttagtgt gaccctgcca tccacctttg cccaattcct tcaacaggtc | 1020 |
| aaaagcgaac tggaaagcaa caatgcgaag aagaatgtcg ttaccttcaa cattgtggat | 1080 |
| ggtaccgtta acggttgggc cgcgggtgag attgcacgtt atgggcctc agacttcgac | 1140 |
| ttttcagaga tttggtggaa agccaatacc tacaacgatc tccgcaatta tatcgaatgg | 1200 |
| ctgcggcaga taacggagg caaacctgta gtgctggctg cctatatgaa ctacaatcaa | 1260 |
| gaatatggac cgatctacga agctgaatcg gccatcctga gtggggtaag tgtcaacacc | 1320 |
| aatcaccccg gctataccgg tactggtttt gttgatggc ttgaaacggt tggcgatagc | 1380 |
| atcacatgga ccattgactt ccccgaaacg ggtgactaca gcttcgtgtt tcgttacgcg | 1440 |
| aatgcaactg gcgcgactgc aacccgcaac gtatatgtag acggtcgtct gttaggccag | 1500 |
| gtatccttcg cgaatcaggt caactgggat acgtgggtgg cggatgcgtg gattcagatt | 1560 |
| gagggcctga ctgccggtac acatagcgtg actctgaaat acgacagcga taatattggg | 1620 |
| gctattaatg ttgaccactt gaccttgggc gaatttgagg aacactcggt tcgcttagct | 1680 |
| gacgccatga tgttcgcgtc tggcgcaacg catattgagc tgggtgatac gaaccagatg | 1740 |
| ttggcgcatg aatactatcc caatcgctcc aaatcgatgc gcaattcact gaaagctgct | 1800 |
| atgcgcgact actactcttt tgccaccgcg tacgaaaacc tgttgtttga tccgaacatt | 1860 |
| gtgcctgctg accaaggtaa ccagtggatt gcgttgacta ccggtcaacc actgtccggg | 1920 |
| aatggtactt ctggcacgat ttggcagatg gtgaagcgta aaagcgatta tgacatcatt | 1980 |

-continued

```
cacttgatca atctgatggg gaacgatgat cagtggcgta acccggcagt tcaaccgacg    2040
tttcagtcaa acattggagt gaaatattat ccgggcccga atgccgcggt cagcggcgtg    2100
tacctggcat cgccagatct ggatcatggg atgactattc cattaatcta tacgacsggg    2160
aatgatagtc gcggcaatta catccagttt acagtcccga gtctgaagta ctgggacatg    2220
atttacgtca aacgcacaat caccacgccg ccggacggtc aatatgaagc ggaatacgcc    2280
atcaaatcgg gtaccaacat caacacggac cataccgggt ataccggttc tggcttcgtc    2340
gacaactttg atgcgtcagg taaaggcgtc agctttatca tcaatgtgcc aacgtccgat    2400
acgtataccc tccgtttccg gtacggtaac ggtggtacaa cgattgcaac gcgcaacctg    2460
tttatcgacg ggcagtatgc gggcaccctg caatttcgca acttgtataa ttgggacgtg    2520
tgggacaccg tagagactac cgtttggctc tcggccggtg tccatcaggt ggtgttatgg    2580
tattcgccgg aaaatgatgg agccatcaat ttggataacc ttatcgtgct gcagcaaacg    2640
acctctgcac gcacttcggc gcgttcgttt tggatgaaca attggtctaa cctgattggg    2700
atccacatgg cgtccaaatt gtctccaacc gataatggca attacggtcc gcgtcttgca    2760
gaacttcact ttcgtggtga ttggccaacc aaccaaattg ttgacgctac cgccttcttc    2820
cgcgacgaaa ccgatctgac gcctattaag tacaccaatg cccacagctt cgacagtgaa    2880
gcgtggttcg agaatgatgg caccctgaca gttcgttatc tgaattacaa tgggagcgct    2940
ctcccggtcc agatcacgaa acagtacgcg atggtaccga atcagaactt cctggttatc    3000
aaatacacct ttctgaacca aacctctaat gcccgcaccc tgaactttct ggaacaagtg    3060
catctgaaca acaaaactag tagcgaccca aacccgggtt ggcagcacgg ctggtgggat    3120
gtgtcacgca acgcactcgg tactgacatg tctcaaaccg gccaattcta tattgaactg    3180
ggagcgtttc agacaatgga ctcatatcaa gtgggaaacg atgcagacag taaccccaac    3240
tcccagacta gcagtccctg gtatcagttt gatgccaatg gcgtcttaaa tcgctgcggc    3300
gatctttggt cgcagaacct gtctatgggc tttcagaaac tgattacggt gccggcgggt    3360
ggtagcgtta cgctggcctt ctattacgcc attggtagca cgcaagaaga ggcagaagcg    3420
gcggcggatt tagcacgcag ccagacagcg gattattggt ttacacaaac cgcagctgaa    3480
tacaataact ggttgaactc tggtcagcgc gttaacacct ccgatattgg gattaatacc    3540
gcgtttgatc gcagcctgat tattaacaaa caggcccaac atcccgaatt tggctcctgg    3600
ccggccgcca ctaaccctag ctaccagtac aaagtatggg tgcgtgattc agcggttaca    3660
gcaatgggca tggatgccgc gaaccatctg tcggaagcgg agaagtactg gaactggatg    3720
gcttcagttc agaatacgga tggcacctgg cataccaact ataatgtctg gaaagcgaac    3780
gaatggatta gcttcgttga accggaacac gatgccattg gcttgtttct gatcggcgtg    3840
tatcagcact attcgctgtt aaaatcccgg gatccttcgg cggcgactac ctttctgaac    3900
aatatttgga cacaggtcac tcgggctggc gattttatct acaagaatat cggcgcttcc    3960
ggttttggac cggctgacgc gtctatctgg gaggaacaag tggaatacaa cattttcacc    4020
caagtaacgt acgccgcagg gctgaatgcg ggccgtttac tggctcagga gaaaggagac    4080
attacccgcg caaacaatta tctcagcggg gcccagatta tcaaagatgc catcctgcgt    4140
agcttcttaa gcagtcctcg cggactctgg aacgaatcga atcgctattt caatcgcgcc    4200
attaacaccg acggcacagc ccgtaccacc gtagatgcgt caagtgacct tatttgggtg    4260
ttcggcctgc tgtcaccgac ggacacacgg attcgtgatc atcgcatcaa ggttctgagt    4320
cgcttgactc atgatcgcta tggtattgcg cgctacgaaa atgacgagtt ttactattcc    4380
```

-continued

```
agtccgtatt caccgggtgg ccagtatgaa gctggggctg cggaaccggt ctggccccag    4440
atgacgatgt acgcatccat gatcgagcat tggcgtgggg atgatgccac ggcattagct    4500
cgtctgaaat ggtatgtgag ccgcactgca cgtggctatg tcaccccctgg tgaggcggtg    4560 gattggacca acggccaacc gctgattagc acggcagtgg aaccggttac tggtagctgg    4620
tttcagatgg ctgtacttac gtatagtaat cagtttgacc cgcgtttgcc agatttctaa    4680
```

<210> SEQ ID NO 3
<211> LENGTH: 807
<212> TYPE: PRT
<213> ORGANISM: Thermoanaerobacter siderophilus

<400> SEQUENCE: 3

```
Gly Gln Tyr Glu Ala Glu Tyr Ala Ile Lys Ser Gly Thr Asn Ile Asn
1               5                   10                  15

Thr Asp His Thr Gly Tyr Thr Gly Ser Gly Phe Val Asp Asn Phe Asp
            20                  25                  30

Ala Ser Gly Lys Gly Val Ser Phe Ile Ile Asn Val Pro Thr Ser Asp
        35                  40                  45

Thr Tyr Thr Leu Arg Phe Arg Tyr Gly Asn Gly Gly Thr Thr Ile Ala
    50                  55                  60

Thr Arg Asn Leu Phe Ile Asp Gly Gln Tyr Ala Gly Thr Leu Gln Phe
65                  70                  75                  80

Arg Asn Leu Tyr Asn Trp Asp Val Trp Asp Thr Val Glu Thr Thr Val
                85                  90                  95

Trp Leu Ser Ala Gly Val His Gln Val Val Leu Trp Tyr Ser Pro Glu
            100                 105                 110

Asn Asp Gly Ala Ile Asn Leu Asp Asn Leu Ile Val Leu Gln Gln Thr
        115                 120                 125

Thr Ser Ala Arg Thr Ser Ala Arg Ser Phe Trp Met Asn Asn Trp Ser
    130                 135                 140

Asn Leu Ile Gly Ile His Met Ala Ser Lys Leu Ser Pro Thr Asp Asn
145                 150                 155                 160

Gly Asn Tyr Gly Pro Arg Leu Ala Glu Leu His Phe Arg Gly Asp Trp
                165                 170                 175

Pro Thr Asn Gln Ile Val Asp Ala Thr Ala Phe Phe Arg Asp Glu Thr
            180                 185                 190

Asp Leu Thr Pro Ile Lys Tyr Thr Asn Ala His Ser Phe Asp Ser Glu
        195                 200                 205

Ala Trp Phe Glu Asn Asp Gly Thr Leu Thr Val Arg Tyr Leu Asn Tyr
    210                 215                 220

Asn Gly Ser Ala Leu Pro Val Gln Ile Thr Lys Gln Tyr Ala Met Val
225                 230                 235                 240

Pro Asn Gln Asn Phe Leu Val Ile Lys Tyr Thr Phe Leu Asn Gln Thr
                245                 250                 255

Ser Asn Ala Arg Thr Leu Asn Phe Leu Glu Gln Val His Leu Asn Asn
            260                 265                 270

Lys Thr Ser Ser Asp Pro Asn Pro Gly Trp Gln His Gly Trp Trp Asp
        275                 280                 285

Val Ser Arg Asn Ala Leu Gly Thr Asp Met Ser Gln Thr Gly Gln Phe
    290                 295                 300

Tyr Ile Glu Leu Gly Ala Phe Gln Thr Met Asp Ser Tyr Gln Val Gly
305                 310                 315                 320
```

```
Asn Asp Ala Asp Ser Asn Pro Asn Ser Gln Thr Ser Ser Pro Trp Tyr
                325                 330                 335
Gln Phe Asp Ala Asn Gly Val Leu Asn Arg Cys Gly Asp Leu Trp Ser
                340                 345                 350
Gln Asn Leu Ser Met Gly Phe Gln Lys Leu Ile Thr Val Pro Ala Gly
                355                 360                 365
Gly Ser Val Thr Leu Ala Phe Tyr Ala Ile Gly Ser Thr Gln Glu
            370                 375                 380
Glu Ala Glu Ala Ala Asp Leu Ala Arg Ser Gln Thr Ala Asp Tyr
385                 390                 395                 400
Trp Phe Thr Gln Thr Ala Ala Glu Tyr Asn Asn Trp Leu Asn Ser Gly
                405                 410                 415
Gln Arg Val Asn Thr Ser Asp Ile Gly Ile Asn Thr Ala Phe Asp Arg
                420                 425                 430
Ser Leu Ile Ile Asn Lys Gln Ala Gln His Pro Glu Phe Gly Ser Trp
                435                 440                 445
Pro Ala Ala Thr Asn Pro Ser Tyr Gln Tyr Lys Val Trp Val Arg Asp
                450                 455                 460
Ser Ala Val Thr Ala Met Gly Met Asp Ala Ala Asn His Leu Ser Glu
465                 470                 475                 480
Ala Glu Lys Tyr Trp Asn Trp Met Ala Ser Val Gln Asn Thr Asp Gly
                485                 490                 495
Thr Trp His Thr Asn Tyr Asn Val Trp Lys Ala Asn Glu Trp Ile Ser
                500                 505                 510
Phe Val Glu Pro Glu His Asp Ala Ile Gly Leu Phe Leu Ile Gly Val
                515                 520                 525
Tyr Gln His Tyr Ser Leu Leu Lys Ser Arg Asp Pro Ser Ala Ala Thr
                530                 535                 540
Thr Phe Leu Asn Asn Ile Trp Thr Gln Val Thr Arg Ala Gly Asp Phe
545                 550                 555                 560
Ile Tyr Lys Asn Ile Gly Ala Ser Gly Phe Gly Pro Ala Asp Ala Ser
                565                 570                 575
Ile Trp Glu Glu Gln Val Glu Tyr Asn Ile Phe Thr Gln Val Thr Tyr
                580                 585                 590
Ala Ala Gly Leu Asn Ala Gly Arg Leu Leu Ala Gln Glu Lys Gly Asp
                595                 600                 605
Ile Thr Arg Ala Asn Asn Tyr Leu Ser Gly Ala Gln Ile Ile Lys Asp
                610                 615                 620
Ala Ile Leu Arg Ser Phe Leu Ser Ser Pro Arg Gly Leu Trp Asn Glu
625                 630                 635                 640
Ser Asn Arg Tyr Phe Asn Arg Ala Ile Asn Thr Asp Gly Thr Ala Arg
                645                 650                 655
Thr Thr Val Asp Ala Ser Ser Asp Leu Ile Trp Val Phe Gly Leu Leu
                660                 665                 670
Ser Pro Thr Asp Thr Arg Ile Arg Asp His Arg Ile Lys Val Leu Ser
                675                 680                 685
Arg Leu Thr His Asp Arg Tyr Gly Ile Ala Arg Tyr Glu Asn Asp Glu
                690                 695                 700
Phe Tyr Tyr Ser Ser Pro Tyr Ser Pro Gly Gly Gln Tyr Glu Ala Gly
705                 710                 715                 720
Ala Ala Glu Pro Val Trp Pro Gln Met Thr Met Tyr Ala Ser Met Ile
                725                 730                 735
Glu His Trp Arg Gly Asp Asp Ala Thr Ala Leu Ala Arg Leu Lys Trp
```

```
            740                 745                 750
Tyr Val Ser Arg Thr Ala Arg Gly Tyr Val Thr Pro Gly Glu Ala Val
        755                 760                 765

Asp Trp Thr Asn Gly Gln Pro Leu Ile Ser Thr Ala Val Glu Pro Val
    770                 775                 780

Thr Gly Ser Trp Phe Gln Met Ala Val Leu Thr Tyr Ser Asn Gln Phe
785                 790                 795                 800

Asp Pro Arg Leu Pro Asp Phe
            805

<210> SEQ ID NO 4
<211> LENGTH: 2424
<212> TYPE: DNA
<213> ORGANISM: Thermoanaerobacter siderophilus

<400> SEQUENCE: 4
```

| | | | | | |
|---|---|---|---|---|---|
| ggtcaatatg | aagcggaata | cgccatcaaa | tcgggtacca | acatcaacac | ggaccatacc | 60 |
| gggtataccg | ttctggcttc | gtcgacaac | tttgatgcgt | caggtaaagg | cgtcagcttt | 120 |
| atcatcaatg | tgccaacgtc | cgatacgtat | accctccgtt | ccggtacgg | taacggtggt | 180 |
| acaacgattg | caacgcgcaa | cctgtttatc | gacgggcagt | atgcgggcac | cctgcaattt | 240 |
| cgcaacttgt | ataattggga | cgtgtgggac | accgtagaga | ctaccgtttg | gctctcggcc | 300 |
| ggtgtccatc | aggtggtgtt | atggtattcg | ccggaaaatg | atggagccat | caatttggat | 360 |
| aaccttatcg | tgctgcagca | aacgacctct | gcacgcactt | cggcgcgttc | gttttggatg | 420 |
| aacaattggt | ctaacctgat | tgggatccac | atggcgtcca | aattgtctcc | aaccgataat | 480 |
| ggcaattacg | gtccgcgtct | tgcagaactt | cactttcgtg | gtgattggcc | aaccaaccaa | 540 |
| attgttgacg | ctaccgcctt | cttccgcgac | gaaaccgatc | tgacgcctat | taagtacacc | 600 |
| aatgcccaca | gcttcgacag | tgaagcgtgg | ttcgagaatg | atggcaccct | gacagttcgt | 660 |
| tatctgaatt | acaatgggag | cgctctcccg | gtccagatca | cgaaacagta | cgcgatggta | 720 |
| ccgaatcaga | acttcctggt | tatcaaatac | acctttctga | accaaacctc | taatgcccgc | 780 |
| accctgaact | ttctggaaca | agtgcatctg | aacaacaaaa | ctagtagcga | cccaaacccg | 840 |
| ggttggcagc | acggctggtg | ggatgtgtca | cgcaacgcac | tcggtactga | catgtctcaa | 900 |
| accggccaat | tctatattga | actgggagcg | tttcagacaa | tggactcata | tcaagtggga | 960 |
| aacgatgcag | acagtaaccc | caactcccag | actagcagtc | cctggtatca | gtttgatgcc | 1020 |
| aatggcgtct | taaatcgctg | cggcgatctt | tggtcgcaga | acctgtctat | gggcttcag | 1080 |
| aaactgatta | cggtgccggc | gggtggtagc | gttacgctgg | ccttctatta | cgccattggt | 1140 |
| agcacgcaag | aagaggcaga | agcggcggcg | gatttagcac | gcagccagac | agcggattat | 1200 |
| tggtttacac | aaaccgcagc | tgaatacaat | aactggttga | actctggtca | gcgcgttaac | 1260 |
| acctccgata | ttgggattaa | taccgcgttt | gatcgcagcc | tgattattaa | caaacaggcc | 1320 |
| caacatcccg | aatttggctc | ctggccggcc | gccactaacc | ctagctacca | gtacaaagta | 1380 |
| tgggtgcgtg | attcagcggt | tacagcaatg | ggcatggatg | ccgcgaacca | tctgtcggaa | 1440 |
| gcggagaagt | actggaactg | gatggcttca | gttcagaata | cggatggcac | ctggcatacc | 1500 |
| aactataatg | tctggaaagc | gaacgaatgg | attagcttcg | ttgaaccgga | acacgatgcc | 1560 |
| attggcttgt | ttctgatcgg | cgtgtatcag | cactattcgc | tgttaaaatc | ccgggatcct | 1620 |
| tcggcggcga | ctacctttct | gaacaatatt | tggacacagg | tcactcgggc | tggcgatttt | 1680 |
| atctacaaga | atatcggcgc | ttccggtttt | ggaccggctg | acgcgtctat | ctgggaggaa | 1740 |

```
caagtggaat acaacatttt cacccaagta acgtacgccg cagggctgaa tgcgggccgt    1800
ttactggctc aggagaaagg agacattacc cgcgcaaaca attatctcag cggggcccag    1860
attatcaaag atgccatcct gcgtagcttc ttaagcagtc ctcgcggact ctggaacgaa    1920
tcgaatcgct atttcaatcg cgccattaac accgacggca cagcccgtac caccgtagat    1980
gcgtcaagtg accttatttg ggtgttcggc ctgctgtcac cgacggacac acggattcgt    2040
gatcatcgca tcaaggttct gagtcgcttg actcatgatc gctatggtat tgcgcgctac    2100
gaaaatgacg agttttacta ttccagtccg tattcaccgg gtggccagta tgaagctggg    2160
gctgcggaac cggtctggcc ccagatgacg atgtacgcat ccatgatcga gcattggcgt    2220
ggggatgatg ccacggcatt agctcgtctg aaatggtatg tgagccgcac tgcacgtggc    2280
tatgtcaccc ctggtgaggc ggtggattgg accaacggcc aaccgctgat tagcacggca    2340
gtggaaccgg ttactggtag ctggtttcag atggctgtac ttacgtatag taatcagttt    2400
gacccgcgtt tgccagattt ctaa                                           2424

<210> SEQ ID NO 5
<211> LENGTH: 45
<212> TYPE: DNA
<213> ORGANISM: Artificial sequence
<220> FEATURE:
<223> OTHER INFORMATION: primer

<400> SEQUENCE: 5
ttctggtctg gtgccacgcg gttctggtca atatgaagcg gaata                    45

<210> SEQ ID NO 6
<211> LENGTH: 45
<212> TYPE: DNA
<213> ORGANISM: Artificial sequence
<220> FEATURE:
<223> OTHER INFORMATION: primer

<400> SEQUENCE: 6
cgagtgcggc cgcaagcttg tcgacttaga aatctggcaa acgcg                    45

<210> SEQ ID NO 7
<211> LENGTH: 20
<212> TYPE: DNA
<213> ORGANISM: Artificial sequence
<220> FEATURE:
<223> OTHER INFORMATION: primer

<400> SEQUENCE: 7
gtcgacaagc ttgcggccgc                                                20

<210> SEQ ID NO 8
<211> LENGTH: 20
<212> TYPE: DNA
<213> ORGANISM: Artificial sequence
<220> FEATURE:
<223> OTHER INFORMATION: primer

<400> SEQUENCE: 8
agaaccgcgt ggcaccagac                                                20

<210> SEQ ID NO 9
<211> LENGTH: 36
<212> TYPE: DNA
<213> ORGANISM: Artificial sequence
<220> FEATURE:
```

```
<223> OTHER INFORMATION: primer

<400> SEQUENCE: 9
actgctcttg gatccggtca atatgaagcg gaatac                                    36

<210> SEQ ID NO 10
<211> LENGTH: 32
<212> TYPE: DNA
<213> ORGANISM: Artificial sequence
<220> FEATURE:
<223> OTHER INFORMATION: primer

<400> SEQUENCE: 10
atggtgatgg tggtggaaat ctggcaaacg cg                                        32

<210> SEQ ID NO 11
<211> LENGTH: 42
<212> TYPE: DNA
<213> ORGANISM: Artificial sequence
<220> FEATURE:
<223> OTHER INFORMATION: primer

<400> SEQUENCE: 11
caccaccatc accatcattg agtcgacctg cagatctcta ga                             42

<210> SEQ ID NO 12
<211> LENGTH: 18
<212> TYPE: DNA
<213> ORGANISM: Artificial sequence
<220> FEATURE:
<223> OTHER INFORMATION: primer

<400> SEQUENCE: 12
ggatccaaga gcagtggc                                                        18
```

ENZYME EXHIBITING ALPHA-1,6-GLUCOSYL TRANSFER ACTIVITY

TECHNICAL FIELD

The present invention relates to an enzyme having α-1,6-glucosyl transfer activity, and an enzyme preparation for manufacturing α-1,6-glucan comprising the enzyme. The present invention relates to a method for manufacturing α-1,6-glucan, comprising the step of allowing the enzyme or the enzyme preparation to act on an oligosaccharide and/or a polysaccharide having an α-1,4-glucosidic bond and/or an α-1,6-glucosidic bond to obtain α-1,6-glucan.

CROSS-REFERENCE TO RELATED APPLICATION

This application is the United States national phase of International Application No. PCT/JP2019/006111 filed Feb. 19, 2019, and claims priority to Japanese Patent Application No. 2018-028272 filed Feb. 20, 2018, the disclosures of which are hereby incorporated by reference in their entirety.

SEQUENCE LISTING

The Sequence Listing associated with this application is filed in electronic format via EFS-Web and is hereby incorporated by reference into the specification in its entirety. The name of the text file containing the Sequence Listing is 8577_2004392_ST25.txt. The size of the text file is 31,941 bytes, and the text file was created on Aug. 19, 2020.

BACKGROUND ART

A saccharide (α-1,6-glucan) which is made of D-glucose units bounded to each other through mainly α-1,6 bonds has been reported to have slow digestibility and sustained digestibility (Patent Document 1). Slowly digestible and sustained digestible saccharides, even when taken, result in a gentle rise in blood sugar level, and thus are useful as saccharides which can be applied even to diabetic patients who need to avoid, for example, a sharp rise in blood sugar level. Further, an isomaltomegalosaccharide having a degree of polymerization (DP) of 10 to 50, among α-1,6-glucans, has been reported to have the effect of increasing the intestinal tract barrier function (Patent Document 2). In addition, an anchor-type isomaltomegalosaccharide having an anchor sugar chain composed of α-1,4 bonds at both terminals or only a non-reducing terminal of an isomaltomegalosaccharide chain (DP: 10 to 100) has the effect of promoting the dissolution of a water-insoluble compound (Patent Document 3). Thus, α-1,6-glucan is expected as a useful saccharide material in various fields including food products and medicine.

As enzymatic methods for manufacturing α-1,6-glucan, disclosed are a method using *Leuconostoc mesenteroides*-derived dextransucrase (Patent Document 4), methods using *Gluconobacter oxydans*-derived dextrin dextranase (Patent Documents 5 and 6), and a method using dextran glucanase derived from a 598K strain belonging to *Paenibacillus* sp. (Patent Document 7).

However, the manufacture method using dextransucrase, as described above, involves the problem that, since only a glucose moiety of a raw material saccharide sucrose is utilized, the dextran yield relative to raw material is not beyond 50%. Although dextrin dextranase and dextran glucanase can use a partially degraded starch product as a substrate, conventional dextrin dextranase was stable only at 45° C. or less, and dextran glucanase was stable only at 50° C. or less (Non-Patent Documents 1 and 2).

REFERENCE LIST

Patent Documents

Patent Document 1: WO2016/047616
Patent Document 1: JP 2015-205856 A
Patent Document 1: JP 2017-114943 A
Patent Document 1: JP H8-173178 A
Patent Document 1: JP 2001-258589 A
Patent Document 1: JP 2007-181452 A
Patent Document 1: JP 2012-095606 A

Non-Patent Documents

Non-Patent Document 1: Masayuki Suzuki et al., J. Appl. Glycosci., 46, pp. 469-473, 1999.
Non-Patent Document 2: Ichinose Hitomi et al., Appl. Microbiol Biotechnol., 101, pp. 4115-4128, 2017.

The entire descriptions of Patent Documents 1 to 7 and Non-Patent Documents 1 and 2 are incorporated herein by reference, especially as disclosures.

SUMMARY OF THE INVENTION

Problem to be Solved by the Invention

In general, heat-resistant enzymes are said to have excellent physicochemical stability as compared with normal enzymes and to be suitable for use on an industrial scale. However, no heat-resistant enzyme acting on a partially degraded starch product and exhibiting α-1,6-glucosyl transfer activity was known. Therefore, a heat-resistant enzyme having α-1,6-glucosyl transfer activity, which is suitable for use on an industrial scale, was demanded.

An object of the present invention is to provide an enzyme having α-1,6-glucosyl transfer activity, which uses a partially degraded starch product as a raw material (substrate) and is heat resistant and suitable for use on an industrial scale; an enzyme preparation for use in manufacturing α-1,6-glucan, comprising the enzyme as an active ingredient; and a method for manufacturing α-1,6-glucan using the enzyme or enzyme preparation.

Means for Solving the Problem

As a result of earnest studies to solve the problems, the present inventors have found an enzyme with α-1,6-glucosyl transfer activity having more heat resistance as compared with conventional enzymes having α-1,6-glucosyl transfer activity, and completed the present invention. The present invention is based on this finding.

The present invention provides the following inventions.

[1] An enzyme having α-1,6-glucosyl transfer activity, which is any one of proteins (a), (b) and (c):
(a) a protein consisting of an amino acid sequence of SEQ ID NO: 3;
(b) a protein consisting of an amino acid sequence having at least 90% amino acid sequence identity to the amino acid sequence of SEQ ID NO: 3; and (c) a protein consisting of an amino acid sequence in which one or several amino acid(s) has/have been substituted, inserted, deleted and/or added in the amino acid sequence of SEQ ID NO: 3.

[2] The enzyme according to [1], which further has α-1,4-glucosyl transfer activity.

[3] An enzyme which is derived from *Thermoanaerobacter siderophilus* and has the following properties:
 (1) having α-1,6-glucosyl transfer activity;
 (2) having α-1,4-glucosyl transfer activity;
 (3) having a molecular weight, as measured by SDS-PAGE, of 80 to 90 kDa;
 (4) having an optimum pH at 4.0 to 5.0;
 (5) being stable within a pH range of 3.5 to 8.5;
 (6) having an optimum temperature at 55 to 60° C.; and
 (7) exhibiting temperature stability at 60° C. or less.

[4] The enzyme according to [3], which (8) acts on maltose, maltotriose, maltotetraose, maltopentaose, isomaltose, isomaltotriose and dextrin as substrates.

[5] An enzyme preparation for manufacturing α-1,6-glucan from an oligosaccharide and/or a polysaccharide having an α-1,4-glucosidic bond and/or an α-1,6-glucosidic bond, which comprises the enzyme according to any one of [1] to [4].

[6] The enzyme preparation according to [5], wherein the oligosaccharide and/or the polysaccharide having the α-1,4-glucosidic bond and/or the α-1,6-glucosidic bond are/is partially degraded starch product(s).

[7] The enzyme preparation according to [5] or [6], wherein the α-1,6-glucan is an isomaltooligosaccharide and/or isomaltomegalosaccharide having a degree of polymerization of 2 to 30.

[8] A composition for catalyzing an α-1,6-glucosyl transfer reaction, comprising any one of proteins (a), (b) and (c):
 (a) a protein consisting of an amino acid sequence of SEQ ID NO: 3;
 (b) a protein consisting of an amino acid sequence having at least 90% amino acid sequence identity to the amino acid sequence of SEQ ID NO: 3; and
 (c) a protein consisting of an amino acid sequence in which one or several amino acid(s) has/have been substituted, inserted, deleted and/or added in the amino acid sequence of SEQ ID NO: 3.

[9] The composition according to [8], which is used for manufacturing α-1,6-glucan from an oligosaccharide and/or a polysaccharide having an α-1,4-glucosidic bond and/or an α-1,6-glucosidic bond.

[10] A method for manufacturing α-1,6-glucan, comprising a reaction step of allowing the enzyme according to any one of [1] to [4], the enzyme preparation according to any one of [5] to [7] or the composition according to [8] or [9] to act on an oligosaccharide and/or a polysaccharide having an α-1,4-glucosidic bond and/or an α-1,6-glucosidic bond to obtain α-1,6-glucan.

[11] The method according to [10], which further comprises, before the above-described reaction step, the step of hydrolyzing starch to obtain the oligosaccharide and/or the polysaccharide having the α-1,4-glucosidic bond and/or the α-1,6-glucosidic bond.

[12] A method for manufacturing a food product, a feed, a bait, a cosmetic product or a pharmaceutical product, comprising the steps of:
 carrying out the method according to [10] or [11] to obtain α-1,6-glucan; and
 using the α-1,6-glucan obtained in above-described step to obtain a food product, a feed, a bait, a cosmetic product or a pharmaceutical product.

[13] A method for manufacturing a glycoside, comprising the step of allowing the enzyme according to any one of [1] to [4], the enzyme preparation according to any one of [5] to [7] or the composition according to [8] or [9] to act on a sugar acceptor and a sugar donor.

[14] The method for manufacturing a glycoside according to [13], wherein the sugar donor is a maltooligosaccharide.

[15] The method for manufacturing a glycoside according to [13] or [14], wherein the sugar acceptor is a compound having an alcoholic hydroxyl group or a compound having a phenolic hydroxyl group.

[16] A method for manufacturing a food product, a feed, a bait, a cosmetic product or a pharmaceutical product, comprising the steps of:
 carrying out the method according to any one of [13] to [15] to obtain a glycoside; and
 using the glycoside obtained in above-described step to obtain a food product, a feed, a bait, a cosmetic product or a pharmaceutical product.

Effect of the Invention

The present invention can provide a novel enzyme having α-1,6-glucosyl transfer activity. According to the present invention, α-1,6-glucan can be manufactured using an enzyme having α-1,6-glucosyl transfer activity, which stably acts within a wide temperature range as compared with conventional enzymes having α-1,6-glucosyl transfer activity. According to the present invention, α-1,6-glucan can be manufactured using a starch hydrolysate as a raw material (substrate).

BRIEF DESCRIPTION OF THE DRAWINGS

Figure 1B:
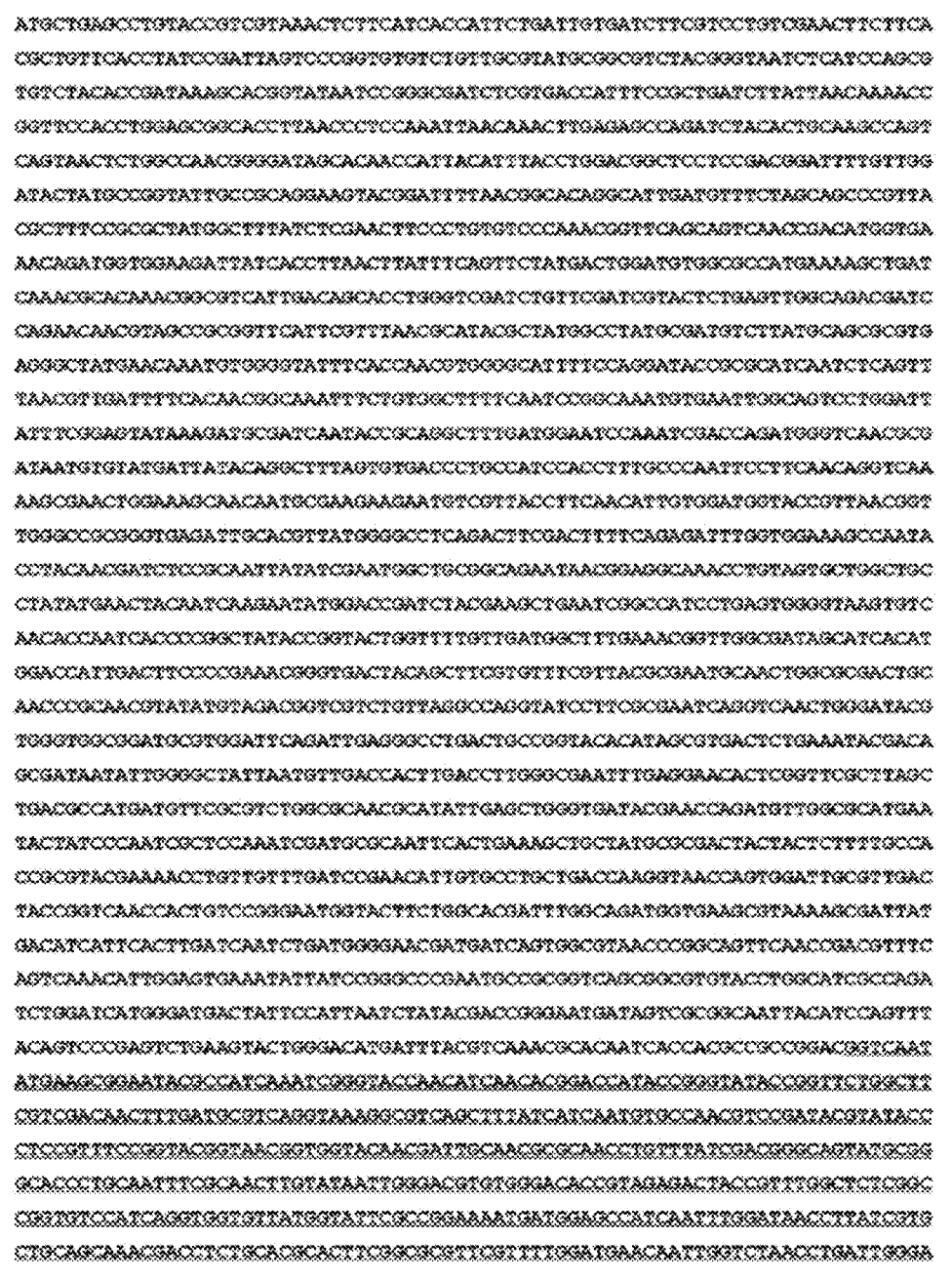

FIG. 1A: An amino acid sequence (SEQ ID NO: 1) of a hypothetical protein derived from *Thermoanaerobacter siderophilus*. The underlined part indicates the $753^{th}$ to $1559^{th}$ amino acids from the N-terminal side.

FIG. 1B: A base sequence (SEQ ID NO: 2) encoding the amino acid sequence of the hypothetical protein derived from *Thermoanaerobacter siderophilus*. The underlined part indicates a portion encoding the $753^{th}$ to $1559^{th}$ amino acids from the N-terminal side of the amino acid sequence in FIG. 1A.

DETAILED DESCRIPTION OF THE INVENTION

Hereinafter, the present invention will be sometimes described based on typical embodiments and specific examples, but is not limited to such embodiments. The numerical ranges expressed using the symbol "−" herein mean ranges including the numerical values indicated before and after the symbol as lower and upper limit values, respectively. The degree of polymerization (DP) described in the present invention means a degree of polymerization of a constituent sugar, glucose, regardless of the type of glucosidic bonds. The sugar composition (%) of a reaction product by the enzyme of the present invention was calculated as an area ratio (%) of a peak corresponding to each saccharide when the total area of peaks detected by HPLC was 100.

(Enzyme and Enzyme Preparation)

The enzyme having α-1,6-glucosyl transfer activity according to the present invention is any one of proteins (a), (b) and (c):

(a) a protein consisting of an amino acid sequence of SEQ ID NO: 3;

(b) a protein consisting of an amino acid sequence having at least 90% amino acid sequence identity to the amino acid sequence of SEQ ID NO: 3; and (c) a protein consisting of an amino acid sequence in which one or several amino acid(s) has/have been substituted, inserted, deleted and/or added in the amino acid sequence of SEQ ID NO: 3.

Figures 1C, 2:
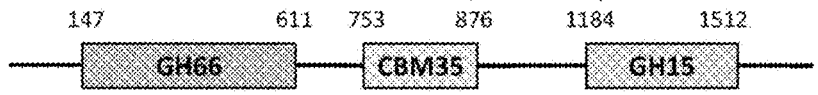
FIG. 1C: The base sequence (SEQ ID NO: 2) encoding the amino acid sequence of the hypothetical protein derived from *Thermoanaerobacter siderophilus* (continuation of FIG. 1B).
FIG. 2: A predicted domain structure of the hypothetical protein derived from *Thermoanaerobacter siderophilus*.

The protein consisting of the amino acid sequence of SEQ ID NO: 3 is obtained by deleting the $1^{st}$ to $752^{th}$ amino acids of an amino acid sequence of SEQ ID NO: 1 acquired from the genome information on the thermophilic bacterium *Thermoanaerobacter siderophilus*, and consists of the $753^{rd}$ to $1559^{th}$ amino acids. Here, the protein consisting of the amino acid sequence of SEQ ID NO: 1 is a hypothetical protein which comprises a sequence annotated with the Glycoside Hydrolase family, but is unknown in specific activity. The hypothetical protein derived from *Thermoanaerobacter siderophilus* is a multi-domain protein comprising a GH66 catalytic domain, a carbohydrate binding module CBM35 and a GH15 catalytic domain in order from the N-terminal side (FIG. 2). The protein consisting of the amino acid sequence of SEQ ID NO: 3 does not comprise a GH66 catalytic domain, but comprises a carbohydrate binding module CBM35 and a GH15 catalytic domain. The protein of the present invention can comprise a carbohydrate binding module CBM35 and a GH15 catalytic domain, i.e., comprise the $753^{th}$ to $1512^{th}$ amino acids of the amino acid sequence of SEQ ID NO: 1. A sequence having two linked active domains of the Glycoside Hydrolase family is not well known, and the actual activity of the hypothetical protein, the function as the entire protein and the interaction between the two active domains are unknown. Therefore, it was unclear whether the protein functions as an enzyme even if only one of the two active domains is expressed.

The present inventors have found that the protein consisting of the amino acid sequence of SEQ ID NO: 3 has α-1,6-glucosyl transfer activity. Here, the "enzyme having α-1,6-glucosyl transfer activity" means an enzyme that catalyzes a reaction for forming an α-1,6-glucosidic bond through a transglucosylation reaction. The α-1,6-glucosyl transfer activity is evaluated by reacting an enzyme with any one of maltose, isomaltose and isomaltotriose as a substrate to obtain a reaction product, and detecting, in the resultant reaction product, a sugar in which glucose has been transferred and extended by an α-1,6 bond from the substrate.

The enzyme of the present invention can have α-1,4-glucosyl transfer activity in addition to the α-1,6-glucosyl transfer activity. Here, the α-1,4-glucosyl transfer activity is an activity of catalyzing a transglucosylation reaction for forming an α-1,4-glucosidic bond. The α-1,4-glucosyl transfer activity is evaluated by reacting an enzyme with any one of maltose, maltotriose, maltotetraose and maltopentaose as a substrate to obtain a reaction product, and detecting, in the resultant reaction product, a sugar in which glucose has been transferred and extended by an α-1,4 bond from the substrate. The present enzyme can further have α-1,4-/α-1,6-glucosidic bond hydrolysis activities, but rarely shows the α-1,4-glucosidic bond hydrolysis activity. Here, the α-1,4-/α-1,6-glucosidic bond hydrolysis activities are activities of catalyzing hydrolysis reactions for cleaving α-1,4-/α-1,6-glucosidic bonds, respectively.

In the enzyme of the present invention, normally, the anomer type of the product is retained for the substrate (anomer retention type). The enzyme of the present invention may mainly exhibit different activities, depending on the type and concentration of the substrate and the reaction time. For example, when the substrate is a maltooligosaccharide (for example, a saccharide having a degree of polymerization of 3 to 5), the enzyme of the present invention sometimes exhibits the α-1,4-glucosyl transfer activity more strongly than the α-1,6-glucosyl transfer activity in the initial stage of the reaction (for example, the reaction time is 15 minutes to about 1 hour under the conditions described in the Examples in the present specification). Even in the case where the substrate is a maltooligosaccharide, the enzyme of the present invention sometimes mainly exhibits the α-1,6-glucosyl transfer activity when the reaction time is longer (for example, the reaction time is 1 hour or more under the conditions described in the Examples in the present specification).

Also, a protein consisting of an amino acid sequence having at least 70%, at least 80%, preferably at least 90%, especially preferably at least 95%, at least 96%, at least 97%, at least 98%, at least 99% amino acid sequence identity to the amino acid sequence of SEQ ID NO: 3 and exhibiting α-1,6-glucosyl transfer activity is also encompassed in the enzyme of the present invention. The amino acid sequence identity is defined as a percent of amino acid residues which are identical between two amino acid sequences to be compared, after alignment of the two amino acid sequences, and, if necessary, introduction of a gap in order to obtain the maximum percent sequence identity. The amino acid sequence identity can be determined, for example, by using publicly available computer software such as BLAST, BLAST-2, ALIGN or Megalign (DNASTAR) software.

Further, a protein consisting of an amino acid sequence in which one or several amino acid(s) has/have been substituted, inserted, deleted and/or added in the amino acid sequence of SEQ ID NO: 3 and having α-1,6-glucosyl transfer activity is also encompassed in the enzyme according to the present invention. The range of the "one or several" in the "amino acid sequence in which one or several amino acid(s) has/have been substituted, inserted, deleted and/or added" referred to herein is not especially limited, and, for example, means around 1 to 20, preferably around 1 to 10, more preferably around 1 to 7, further preferably around 1 to 5, especially preferably around 1 to 3.

As for a method for manufacturing the enzyme of the present invention, see the section <Manufacture of enzyme> which will be given below.

The enzyme of the present invention is an enzyme which is derived from *Thermoanaerobacter siderophilus* and has the following properties:
 (1) having α-1,6-glucosyl transfer activity;
 (2) having α-1,4-glucosyl transfer activity;
 (3) having a molecular weight, as measured by SDS-PAGE, of 80 to 90 kDa;
 (4) having an optimum pH at 4.0 to 5.0;
 (5) being stable within a pH range of 3.5 to 8.5;
 (6) having an optimum temperature at 55 to 60° C.; and
 (7) exhibiting temperature stability at 60° C. or less.

The enzyme of the present invention further has the following property:
 (8) acting on maltose, maltotriose, maltotetraose, maltopentaose, isomaltose, isomaltotriose and dextrin as substrates.

The α-1,6-glucosyl transfer activity of the present enzyme is determined by reacting the enzyme of the present invention with any one of maltose, isomaltose and isomaltotriose as a substrate to obtain a reaction product, and detecting, in the resultant reaction product, a sugar in which glucose has been transferred and extended by an α-1,6 bond from the substrate. The α-1,4-glucosyl transfer activity of the enzyme is determined by reacting the enzyme of the present invention with any one of maltose, maltotriose, maltotetraose se and maltopentaose as a substrate to obtain a reaction product, and detecting, in the resultant reaction product, a sugar in which glucose has been transferred and extended by an α-1,4 bond from the substrate.

The present enzyme can have α-1,6-glucosidic bond hydrolysis activity. The α-1,6-glucosidic bond hydrolysis activity of the present enzyme is determined by reacting the enzyme of the present invention with any one of isomaltotetraose, isomaltopentaose, isomaltohexaose and dextran as a substrate and detecting glucose.

The present enzyme has a molecular weight, as measured by SDS-PAGE, of 80 to 90 kDa. It should be noted that the molecular weight herein is indicated for the protein which is expressed and secreted using *Bacillus subtilis* as a host cell based on plasmid recombination. The present enzyme having a molecular weight measured to be 80 to 90 kDa in Example 2 is a protein which has His-Tag (six histidines added) on the C-terminal side and in which a secretion signal composed of predicted 17 amino acids has been cleaved. When the protein is secreted extracellularly, the secretion signal is cleaved, but the cleavage site is somewhat shifted in some cases. The actual cleavage site has not been confirmed, but it is inferred that the secretion signal has been cleaved in a range of several amino acids from an amino acid having a high cleavage site score predicted by the signal peptide prediction server SignalP4.1. In a preferred embodiment of the present invention, the enzyme of the present invention has a molecular weight, as measured by SDS-PAGE, of 75 to 92 kDa. In a more preferred embodiment of the present invention, the enzyme of the present invention has a molecular weight, as measured by SDS-PAGE, of 80 to 90 kDa.

The enzyme of the present invention exhibits the maximum activity at a pH of 4.5 when measured at a temperature of 37° C., and has an optimum pH at 4.0 to 5.0. Also, the present enzyme was stable at a pH of 3.5 to 8.5 in a test in which it was retained at a temperature of 4° C. for 24 hours. The optimum pH and pH stability were determined when the maltose degradation activity was measured under the conditions indicated in Example 4.

The enzyme of the present invention exhibits the maximum activity at a temperature of 60° C. when measured at a pH of 4.5, and has an optimum temperature at 55 to 60° C. Also, the present enzyme was stable at 60° C. or less in a test in which it was retained at a pH of 4.5 for 15 minutes. The optimum temperature and temperature stability were determined when the maltose degradation activity was measured under the conditions indicated in Example 4. The optimum pH and temperature and the pH and temperature stabilities were determined by measuring the maltose degradation activity based on the amount of glucose produced using maltose as a substrate. With the present enzyme, the degradation of maltose into glucose may take place by an α-1,4-glucosyl transfer reaction, an α-1,6-glucosyl transfer reaction and an α-1,4-glucosidic bond hydrolysis reaction. Since almost the same catalytic site is considered to be involved in the α-1,4-glucosyl transfer activity, the α-1,6-glucosyl transfer activity and the α-1,4-glucosidic bond hydrolysis activity, the enzyme is considered to exhibit similar reaction properties (the optimum pH and temperature and the pH and temperature stabilities) in either case. Therefore, the maltose degradation activity was used to evaluate the reaction properties.

A conventional enzyme having α-1,6-glucosyl transfer activity, for example, dextrin dextranase derived from *Gluconobacter oxydans*, exhibits the maximum activity at a pH of 5.2 and a temperature of 38° C., and exhibits temperature stability at 45° C. or less. Further, dextran glucanase derived from a 598K strain belonging to *Paenibacillus* sp. exhibits temperature stability at 50° C. or less. Thus, the enzyme of the present invention exhibits high heat resistance and has stability suitable for use on an industrial scale as compared with such conventional enzymes having α-1,6-glucosyl transfer activity.

The enzyme of the present invention can act on maltose, maltotriose, maltotetraose, maltopentaose, isomaltose, isomaltotriose and dextrin, without limitation thereto, as substrates.

The enzyme preparation of the present invention is an enzyme preparation for manufacturing α-1,6-glucan from an oligosaccharide and/or a polysaccharide having an α-1,4-glucosidic bond and/or an α-1,6-glucosidic bond, which comprises the enzyme having α-1,6-glucosyl transfer activity according to the present invention. Specifically, the enzyme preparation of the present invention is brought in contact with an oligosaccharide and/or a polysaccharide having an α-1,4-glucosidic bond and/or an α-1,6-glucosidic bond in a reaction solution under conditions suitable for exhibition of the α-1,6-glucosyl transfer activity of the enzyme, so that glucose is transferred and extended by an α-1,6 bond due to the α-1,6-glucosyl transfer effect of the enzyme, with the result that α-1,6-glucan is obtained.

Examples of the oligosaccharide and/or the polysaccharide having the α-1,4-glucosidic bond and/or the α-1,6-glucosidic bond, which is the substrate of the present invention, can include maltooligosaccharides, isomaltooligosaccharides and dextrins. As used herein, the "oligosaccharide" means a saccharide in which 2 to 10 monosaccharide molecules bind to each other through glucosidic bonds, and the "polysaccharide" means a saccharide in which many, specifically, more than 10, monosaccharide molecules are polymerized by glucosidic bonds. The maltooligosaccharide is a saccharide having a degree of polymerization of 2 to 10 in which glucoses bind to each other through α-1,4 bonds, and includes maltose, maltotriose, maltotetraose, maltopentaose and maltohexaose. The isomaltooligosaccharide is a saccharide having a degree of polymerization of 2 to 10 in which glucoses bind to each other through α-1,4 bonds and α-1,6 bonds and in which glucoses bind to each other only through α-1,6 bonds, and includes isomaltose, panose, isomaltotriose, isomaltotetraose and isopanose. The dextrin is obtained by partially hydrolyzing starch, and is obtained as a mixture of saccharides having various degrees of polymerization in which glucoses bind to each other through α-1,4 bonds and α-1,6 bonds. In general, the dextrin is sometimes differentiated as follows: those having a dextrose equivalent (DE) of 10 or more and 20 or less is referred to as maltodextrins, and those having a DE of less than 10 is referred to simply as dextrins. However, the term "dextrin" is used herein to mean a product obtained by lowering the molecular weight of starch regardless of the DE range, and is used as a term including maltodextrin.

When the enzyme or enzyme preparation of the present invention or a composition which will be described later is used to produce α-1,6-glucan, a partially degraded starch product can be utilized as a raw material. This is because the partially degraded starch product is composed mainly of dextrin and comprises a maltooligosaccharide and an isomaltooligosaccharide in a part thereof. The partially degraded starch product can be obtained by hydrolyzing starch with an acid or enzyme and optionally separating/purifying the resultant starch hydrolysate.

The α-1,6-glucan produced by using the enzyme or enzyme preparation of the present invention or the composition which will be described later is an oligosaccharide or polysaccharide having a degree of polymerization of 2 or more, which is composed of glucose as a constituent sugar and has an α-1,6-glucosidic bond. Briefly, the α-1,6-glucan may have α-1,2-, α-1,3- and α-1,4-glucosidic bonds in addition to the α-1,6-glucosidic bond. The α-1,6-glucan of the present invention will be described in detail later.

(Composition)

The present invention provides a composition for catalyzing an α-1,6-glucosyl transfer reaction, comprising any one of proteins (a), (b) and (c):

(a) a protein consisting of an amino acid sequence of SEQ ID NO: 3;

(b) a protein consisting of an amino acid sequence having at least 90% amino acid sequence identity to the amino acid sequence of SEQ ID NO: 3; and (c) a protein consisting of an amino acid sequence in which one or several amino acid(s) has/have been substituted, inserted, deleted and/or added in the amino acid sequence of SEQ ID NO: 3.

The protein consisting of the amino acid sequence of SEQ ID NO: 3, which is contained in the composition, is similar to that described in the section (Enzyme and enzyme preparation). For example, the protein contained in the composition may be a protein consisting of an amino acid sequence having at least 70%, at least 80%, preferably at least 90%, especially preferably at least 95%, at least 96%, at least 97%, at least 98%, at least 99% amino acid sequence identity to the amino acid sequence of SEQ ID NO: 3, and exhibiting α-1,6-glucosyl transfer reaction activity. Further, the protein contained in the composition may be a protein consisting of an amino acid sequence in which one or several amino acid(s) has/have been substituted, inserted, deleted and/or added in the amino acid sequence of SEQ ID NO: 3 and having α-1,6-glucosyl transfer reaction activity.

The protein contained in the composition can be derived from *Thermoanaerobacter siderophilus* and have any one of the following properties:

(1) having α-1,6-glucosyl transfer activity;
(2) having α-1,4-glucosyl transfer activity;
(3) having a molecular weight, as measured by SDS-PAGE, of 80 to 90 kDa;
(4) having an optimum pH at 4.0 to 5.0;
(5) being stable within a pH range of 3.5 to 8.5;
(6) having an optimum temperature at 55 to 60° C.;
(7) exhibiting temperature stability at 60° C. or less; and
(8) acting on maltose, maltotriose, maltotetraose, maltopentaose, isomaltose, isomaltotriose and dextrin as substrates.

The composition can be used for manufacturing α-1,6-glucan from an oligosaccharide and/or a polysaccharide having an α-1,4-glucosidic bond and/or an α-1,6-glucosidic bond. The α-1,6-glucan can be manufactured based on a method for manufacturing α-1,6-glucan which will be described later.

The composition of the present invention can comprise additional components in addition to the protein, as long as the additional components do not inhibit an α-1,6-glucosyl transfer reaction. These components may be those used in common enzyme compositions, such as a buffer, a stabilizer and an excipient. Such additional components are known from the prior art, and also well known to those skilled in the art. The form of the composition of the present invention is also not particularly limited, and can be solid (for example, powdery) or liquid. The composition of the present invention can be used, for example, by being added, in a solid or liquid form, to a substrate solution.

(Method for Manufacturing α-1,6-Glucan)

The method for manufacturing α-1,6-glucan according to the present invention comprises a reaction step of allowing the enzyme, enzyme preparation or composition of the present invention to act on an oligosaccharide and/or a polysaccharide having an α-1,4-glucosidic bond and/or an α-1,6-glucosidic bond to obtain α-1,6-glucan. Specifically, the enzyme, enzyme preparation or composition of the present invention is brought in contact with an oligosaccharide and/or a polysaccharide having an α-1,4-glucosidic bond and/or an α-1,6-glucosidic bond in a reaction solution under conditions suitable for exhibition of the α-1,6-glucosyl transfer activity of the enzyme, so that glucose is transferred and extended by an α-1,6 bond due to the α-1,6-glucosyl transfer effect of the enzyme, with the result that α-1,6-glucan can be manufactured.

Examples of the oligosaccharide and/or the polysaccharide having the α-1,4-glucosidic bond and/or the α-1,6-glucosidic bond, which are/is the substrate(s) used in the method for manufacturing α-1,6-glucan of the present invention, can include maltooligosaccharides, isomaltooligosaccharides and dextrins. The maltooligosaccharide, isomaltooligosaccharide and dextrin are as explained above. The maltooligosaccharide and isomaltooligosaccharide may be those at a high-purity reagent level or those having low purity such as maltooligosaccharide syrup. Examples of the maltooligosaccharide which can be used in the present invention include, but are not limited to, Fujioligo #360 and Fujioligo #450 (Nihon Shokuhin Kako Co., Ltd.). Examples of the isomaltooligosaccharide which can be used in the present invention include, but are not limited to, Isomalto 500 and Isomalto 900 (Showa Sangyo Co., Ltd.). Examples of the dextrin which can be used in the present invention include, but are not limited to, Pinedex #1, Pinedex #2, Pinedex #4, Pinedex #6 and Pinedex #100 (Matsutani Chemical Industry Co., Ltd.). The substrate concentration can be within the range of 0.1 to 40% (w/w) in the reaction solution, but is not limited thereto. Since a higher substrate concentration provides a higher sugar transfer activity, the substrate concentration is preferably higher from the viewpoint of obtaining a higher-concentration α-1,6-glucan. In general, the substrate concentration is preferably higher also from the viewpoint that the heat resistance of the enzyme is improved in the presence of the substrate.

The method for manufacturing α-1,6-glucan according to the present invention can comprise, before the above-described reaction step, the step of hydrolyzing starch to obtain the oligosaccharide and/or the polysaccharide having the α-1,4-glucosidic bond and/or the α-1,6-glucosidic bond, according to need. In this step, starch is hydrolyzed with an acid or enzyme by a conventional method, and the resultant starch hydrolysate is separated/purified, according to need, to obtain maltooligosaccharide, isomaltooligosaccharide and dextrin, which are the oligosaccharides and/or the polysaccharides having the α-1,4-glucosidic bond and/or the α-1,6-glucosidic bond. In this step, the degree of hydrolysis of starch can appropriately be adjusted. The degree of hydrolysis can be expressed by the dextrose equivalent (DE). The DE of the starch hydrolysate in this step is not limited to, but is sufficiently 2 to 70, and can be adjusted to a DE suitable for the degree of polymerization of the α-1,6-glucan which is desired to be manufactured in the subsequent reaction step.

Also, a short-chain-length amylose can be used as the starch hydrolysate.

By the manufacture method of the present invention, α-1,6-glucan having a degree of polymerization of 2 to 30 can be manufactured. The α-1,6-glucan having a degree of polymerization of 2 to 30 is manufactured as a mixture of saccharides containing a large amount of α-1,6-glucan having a degree of polymerization of 2 to 30. The composition of this mixture varies depending on various reaction conditions, for example, the type and concentration of the substrate, the reaction time, whether any other enzyme is used or not, and, if such an enzyme is used, the type thereof. In a preferred embodiment, the composition of the α-1,6-glucan manufactured in the present invention comprises saccharides having a DP of 3 to 30 in a proportion of 70% or more, and, especially, can comprise such saccharides in a proportion of 80% or more. In a preferred embodiment, the composition of the α-1,6-glucan manufactured in the present invention can comprise saccharides having a DP of 10 to 30 in a proportion of 30% or more, especially 40% or more, further 50% or more.

The α-1,6-glucan which can be manufactured in the present invention may be an isomaltooligosaccharide and/or an isomaltomegalosaccharide. The isomaltooligosaccharide is a saccharide with a degree of polymerization of 2 to 10 in which glucoses bind to each other in a binding mode including an α-1,6 bond, and the isomaltomegalosaccharide is a saccharide with a degree of polymerization of 10 to 100 in which glucoses bind to each other in a binding mode including an α-1,6 bond. In particular, the α-1,6-glucan which can be manufactured in the present invention is preferably an isomaltooligosaccharide and/or an isomaltomegalosaccharide having a degree of polymerization of 2 to 30. The enzyme, enzyme preparation or composition of the present invention is used, and the type and concentration of the substrate, the reaction conditions and the like are adjusted, thereby making it possible to manufacture an isomaltooligosaccharide and/or an isomaltomegalosaccharide having the desired degree of polymerization.

In a preferred embodiment, α-1,6-glucan having a high content proportion of saccharides having a degree of polymerization of 10 to 30 can be manufactured by the manufacture method of the present invention. The substrate to be used in this case is preferably a maltooligosaccharide or isomaltooligosaccharide having a degree of polymerization of 2 to 10, and, especially, is more preferably a maltooligosaccharide or isomaltooligosaccharide having a degree of polymerization of 5 to 10. In another preferred embodiment, α-1,6-glucan having a high content proportion of saccharides having a degree of polymerization of 10 to 30 can be manufactured by using dextrin as the substrate in the manufacture method of the present invention. The substrate to be used in this case is preferably dextrin having a DE of around 3 to 30, more preferably dextrin having a DE of around 4 to 20. In still another preferred embodiment, α-1,6-glucan having a high content proportion of saccharides having a degree of polymerization of 2 to 10 can be manufactured by the manufacture method of the present invention.

In the reaction step of the manufacture method according to the present invention, the enzyme, enzyme preparation or composition of the present invention and any other enzyme can be used in combination. Any other enzyme can be used in combination with the enzyme, enzyme preparation or composition of the present invention for the purpose, but which is not limited thereto, of increasing a partially degraded starch product which can serve as the substrate of the enzyme and enhancing the efficiency of glucose transfer and extension by the α-1,6 bond and the yield of the α-1,6-glucan.

Any other enzyme can be used for the purpose, but which is not limited thereto, of cleaving the α-1,4 bond and/or the α-1,6 bond of the oligosaccharide and/or the polysaccharide having the α-1,4-glucosidic bond and/or the α-1,6-glucosidic bond. Especially when the degree of degradation of the partially degraded starch product is low, any other enzyme can be used for the purpose of cleaving the α-1,4 bond and/or the α-1,6 bond of saccharides having a high degree of polymerization. Although the present invention is not limited by any specific theory, this is because the cleavage of the α-1,4 bond and/or the α-1,6 bond of the partially degraded starch product is considered to increase the partially degraded starch product which can serve as the substrate of the present enzyme, so that the glucose transfer and extension by an α-1,6 bond due to the present enzyme effectively take place.

Examples of any other enzyme include, but are not limited to, α-amylase, isoamylase and pullulanase. The origins of and preparation methods for α-amylase, isoamylase and pullulanase used in the present invention are not particularly limited. The α-amylase is an enzyme that cleaves an α-1,4 bond of starch or the like to degrade the starch into a polysaccharide, an oligosaccharide or maltose. The isoamylase is an enzyme that cleaves an α-1,6 bond of starch or the like, and the pullulanase is an enzyme that cleaves an α-1,6 bond of pullulan (a polysaccharide containing repeats of an α-1,4 bond, an α-1,4 bond and an α-1,6 bond). The enzyme of the present invention and any other enzyme as described above are allowed to act, in combination, on the partially degraded starch product, thereby making it possible to effectively obtain α-1,6-glucan in a high yield.

The concentrations (number of units) of the enzyme of the present invention used in the above-described reaction step and, if combined, the α-amylase, isoamylase and/or pullulanase in a reaction solution can appropriately be determined, for example, in consideration of the type (i.e., degree of degradation) of the partially degraded starch product which is the substrate and the concentration thereof in the reaction solution, and further the length of the reaction time. When other enzymes are used in combination, the concentration ratio between the enzyme of the present invention and the α-amylase, isoamylase and pullulanase can also be appropriately determined according to the type of the partially degraded starch product which is the substrate, and the origins and performances of the respective enzymes.

The reaction temperature in the above-described reaction step is not particularly limited, as long as it falls within a temperature range in which the enzyme of the present invention acts stably. To enhance the α-1,6-glucan synthesis efficiency, the reaction temperature is preferably set within a temperature range in which the enzyme of the present invention having α-1,6-glucosyl transfer activity acts more efficiently. The enzyme having α-1,6-glucosyl transfer activity according to the present invention is stable at least at a temperature of 60° C. or less, when the pH ranges from 3.5 to 8.0. Accordingly, the temperature of the reaction system in which the present enzyme is used can be set, for example, within a wide temperature range of 35 to 60° C. Although precise temperature management is sometimes difficult in the reaction system on an industrial scale, the present enzyme is advantageous in that it can be used stably within a wide temperature range.

The above-described reaction step can be carried out at a reaction temperature of 35 to 60° C., but the reaction temperature is preferably 40 to 60° C., more preferably 50 to 60° C. This is because the enzyme of the present invention exhibits high temperature stability, and exhibits high activity also within a temperature range of 50 to 60° C.

When any other enzyme is used in combination, the reaction temperature in the above-described reaction step has only to fall within a temperature range in which the enzyme of the present invention and α-amylase, isoamylase and/or pullulanase act stably. Since the enzyme of the present invention is stable within a wide temperature range as described above, the temperature can often be set within a range in which the activities of all the enzymes used in the reaction system can be utilized sufficiently, in view of the temperatures at which any other enzyme to be used in combination is activated stably.

The reaction temperature does not have to be constant through the entire reaction time, and can appropriately be adjusted as follows. In the case where it is desired to enhance the activity of any other enzyme to be used in combination in the initial stage of the reaction time, the temperature in the initial stage of the reaction is set within a temperature range in which the activity of the enzyme increases. In the medium and later stages of the reaction time, the temperature is set within a temperature range in which the activity of the enzyme of the present invention increases.

The reaction time in the above-described reaction step can appropriately be determined, for example, in consideration of the reaction temperature, the substrate concentration, and, when any other enzyme is used in combination, the activity of the enzyme used. The enzyme, enzyme preparation or composition of the present invention sometimes exhibits the α-1,4-glucosyl transfer activity more strongly than the α-1,6-glucosyl transfer activity in the initial stage of the reaction (for example, the reaction time is 15 minutes to about 1 hour under the conditions described in the Examples in the present specification). On the other hand, the enzyme, enzyme preparation or composition of the present invention sometimes exhibits the α-1,6-glucosyl transfer activity strongly in the medium stage of the reaction (for example, the reaction time is 1 hour or more under the conditions described in the Examples in the present specification). On the other hand, the enzyme, enzyme preparation or composition of the present invention sometimes exhibits the hydrolysis activity strongly in the later stage of the reaction (for example, the reaction time is 6 hour or more under the conditions described in the Examples in the present specification). Based on the conventional techniques in the art, a reaction time suitable for manufacturing α-1,6-glucan can appropriately be determined.

An aqueous solution containing α-1,6-glucan is obtained through the reaction in the above-described reaction step. From this aqueous solution, α-1,6-glucan can be purified by using, for example, a precipitation method by an organic solvent using ethanol or the like, a chromatographic fractionation method, or treatment with an ultrafiltration membrane. According to these methods, α-1,6-glucan can be purified more efficiently through a single operation or a combination of some operations.

The method for manufacturing a food product, a feed, a bait, a cosmetic product or a pharmaceutical product according to the present invention can comprise the steps of: allowing the enzyme having α-1,6-glucosyl transfer activity according to the present invention to act on an oligosaccharide and/or a polysaccharide having an α-1,4-glucosidic bond and/or an α-1,6-glucosidic bond to manufacture α-1,6-glucan, and using the α-1,6-glucan manufactured in the above-described step to obtain a food product, a feed, a bait, a cosmetic product or a pharmaceutical product.

The step of allowing the enzyme having α-1,6-glucosyl transfer activity according to the present invention to act on an oligosaccharide and/or a polysaccharide having an α-1,4-glucosidic bond and/or an α-1,6-glucosidic bond to manufacture α-1,6-glucan, thereby obtaining the α-1,6-glucan can be carried out based on the method for manufacturing α-1,6-glucan described above.

In the step of using the α-1,6-glucan manufactured in the above-described step to obtain a food product, a feed, a bait, a cosmetic product or a pharmaceutical product, it is possible to use the α-1,6-glucan of the present invention as one of raw materials to manufacture a food product, a feed, a bait, a cosmetic product or a pharmaceutical product, or to prepare the α-1,6-glucan itself into an appropriate form (powder, liquid or the like) to provide it as a food product, a feed, a bait, a cosmetic product or a pharmaceutical product.

The method for manufacturing a glycoside according to the present invention is a method for manufacturing a glycoside, comprising the step of allowing the enzyme, enzyme preparation or composition of the present invention to act on a sugar acceptor and a sugar donor. A microorganism which expresses the enzyme of the present invention may be allowed to act on the sugar acceptor and the sugar donor. The present enzyme can be allowed to act on a solution containing the sugar donor and the sugar acceptor to prepare a glycoside in which at least one glycosyl group has been transferred to the sugar acceptor. The method for manufacturing a glycoside according to the present invention can be carried out while the reaction temperature and pH are appropriately set based on the method for manufacturing α-1,6-glucan described above. In the method for manufacturing a glycoside according to the present invention, the reaction temperature can be adjusted according to the properties of the sugar acceptor. The present enzyme can be used stably within a wide temperature range, and thus can be used to manufacture various glycoside compounds.

The sugar donor may be any compound as long as it is a compound from which glycosyl is transferred by the enzyme, enzyme preparation or composition of the present invention. More specifically, maltooligosaccharides are indicated as the sugar donor, and maltose and maltotriose are preferred.

The glycoside manufactured by the method of the present invention can have a glycosidic bond between its sugar moiety and a binding site of non-sugar compound.

The sugar acceptor may be any compound as long as it is a compound having a hydroxyl group to which a glycosyl group is transferred by the enzyme, enzyme preparation or composition of the present invention. Specifically, alcohols (for example, ethanol, 1-propanol, 2-propanol, L-menthol, 1-butanol and 2-butanol); polyols (for example, glycerol and propylene glycol); vitamins (for example, L-ascorbic acid, retinol, inositol and tocopherol); flavonoids (for example, quercetin, catechin, rutin and hesperidin); phenol derivatives (for example, hydroquinone), and the like can be used. The sugar acceptor is not particularly limited as long as it is a compound having a hydroxyl group. When the sugar acceptor is easily oxidized, it is also effective to preliminarily add a reducing agent to the reaction system, according to need.

The glycoside manufactured by using the enzyme, enzyme preparation or composition of the present invention can be used as one of raw materials for a food product, a feed, a bait, a cosmetic product or a pharmaceutical product, and can also be provided, as it is, as a food product, a feed, a bait, a cosmetic product or a pharmaceutical product. The glycoside manufactured by using the enzyme, enzyme preparation or composition of the present invention is easily dissolved in water, can exist as a solid powder at room temperature, and further is stable in quality, and thus can be widely utilized in foods and beverages, pharmaceutical products, cosmetic products and the like.

Examples of the food product to be manufactured by the method for manufacturing a food product according to the present invention include, but are not limited to: various carbohydrates (bread, noodles, boiled rice, and rice cakes); various Japanese-style confectionery (rice crackers, cubic rice crackers, millet-and-rice cakes, Turkish delight (gyuhi), rice cakes, buns with a beam jam filling, bean-jam pancakes, sweet rice jelly, sweet bean paste, sweet jelly of adzuki beans, soft adzuki-bean jelly, Japanese agar jelly (kingyoku), sponge cakes called Castella, and hard candies); various Western-style confectionery (bread, biscuits, crackers, cookies, pies, doughnuts, steamed cakes, puddings, jelly, mousse, bavarois, custard cream, cream puff, waffles, sponge cakes, chocolates, chewing gums, caramels, nougat, candies, and syrups); various ices (ice cream, sherbet, gelato, and shaved ice); various pasty foods (flour paste, peanut paste, margarine, and fruit paste); various beverages (fruit juice-containing beverages, fruit juice, vegetable juice, cider, ginger ale, isotonic beverages, amino acid beverages, jelly beverages, coffee beverages, green tea, black tea, oolong tea, barley tea, milk beverages, lactic acid bacteria beverages, cocoa, beer, low-malt beer, quasi-beer, non-alcoholic beverages, beer-flavored beverages, liqueur, shochu-based beverages, refined sake, fruit liquor, distilled liquor, nutritional drinks, healthy beverages, and powdered drinks); fruit and vegetable processed products (jams, marmalades, fruit and vegetable in syrup, candied fruits, and pickles); various dairy products (cheese, yogurt, butter, condensed milk, and dry milk powder); powdered foods (powdered soup, powdered mousse, powdered jelly, and powdered sweeteners); nutritional foods; diet foods; nutritional foods for sports; fluid diets; semi-solid fluid diets; care foods; and swallowing food.

Examples of the feed and bait to be manufactured by the method for manufacturing a food product according to the present invention include, but are not limited to, feeds and baits for livestock, poultry, fish and shellfish, and insects (honeybee, silkworm, etc.). Their form includes a powder, a pellet, a tablet, a paste bait and a capsule.

Examples of the cosmetic product to be manufactured by the method for manufacturing a food product according to the present invention include, but are not limited to, moisturizers and cosmetic agents. Their form includes a milky lotion, a cream and an emulsion.

Examples of the pharmaceutical product to be manufactured by the method for manufacturing a food product according to the present invention include, but are not limited to, antiobesity agents and blood glucose level elevation inhibitors. Their form includes a tablet, a powder agent, a liquid agent and a capsule agent.

<Manufacture of Enzyme>

The enzyme of the present invention is not particularly limited, and may be a protein synthesized by chemical synthesis or a recombinant protein prepared by a gene recombination technique. Hereinafter, the case where a recombinant protein is prepared will be described.

The enzyme of the present invention having an amino acid sequence of SEQ ID NO: 3 or an amino acid sequence having at least 90% amino acid sequence identity to the amino acid sequence of SEQ ID NO: 3 can be prepared by a gene engineering technique. For example, the gene encoding the amino acid sequence of SEQ ID NO: 3 can produced by transforming a host cell with a DNA molecule (especially, in a form of being inserted into an expression vector) which can be replicated in the host cell or which is incorporated into a chromosome and comprises the gene in an expressible state, and culturing the host cell. This DNA molecule can be obtained by incorporating, into a vector molecule, a DNA fragment encoding the amino acid sequence of SEQ ID NO: 3 or the amino acid sequence having at least 90% amino acid sequence identity to the amino acid sequence of SEQ ID NO: 3. According to a preferred embodiment of the present invention, this vector is a plasmid. The production of the DNA molecule in the present invention can be carried out in accordance with the method described in Molecular Cloning: A Laboratory Manual.

The vector which can be utilized in the present invention can appropriately be selected from a virus, a plasmid, a cosmid vector and the like, in consideration of the type of the host cell used. For example, the vector includes, but is not limited to, pJEXOPT2 (see JP 2009-17841 A) and pHT plasmids when the host cell is *Bacillus subtilis*; λ-phage bacteriophage, pET, pUC, pCold and pGEX plasmids when the host cell is *E. coli*; YEp, YCp and YIP vectors when the host cell is yeast; or pLeu4, pPPLeu4 and pJPLeu types (which are described in JP H4-218382 A). The plasmids may each contain a marker for selecting a transformant, and usable selection markers can be, but are not limited to, drug resistance marker and auxotrophic marker genes.

Further, the expression vector which can be used in the present invention can have DNA sequences necessary for expression of the enzyme gene, for example, a transcriptional regulation signal such as a promoter, a terminator, a ribosome-binding site, and a transcription termination signal, and a translation regulation signal. Promoters of subtilisin and SPAC can be used in *Bacillus subtilis*, and promoters of alcohol dehydrogenase (ADH), acid phosphatase (PHO), galactose gene (GAL) and glyceraldehyde-3-phosphate dehydrogenase gene (GAP) can be used in yeast, though the promoter is not limited thereto. The signal peptide is preferably used as having the advantage of facilitating purification from the culture supernatant. The signal peptide can be replaced with one derived from *Bacillus subtilis* or yeast (for example, invertase signal, acid phosphatase signal or λ-factor signal). Also, contrivance to increase the expression efficiency, e.g., simultaneous expression of a molecule chaperon using a cspA promoter or the like in addition to commonly and conventionally used lac promoter and T7 promoter, can be applied to *E. coli*.

The transformed host cell can be cultured by a common method for the host cell used. Normally, the enzyme is produced and accumulated in an intracellular or extracellular culture by culturing the host cell for around 1 to 4 day(s). As for culture conditions (medium, pH, temperature, etc.), a common temperature is, for example, 25 to 37° C. for bacteria, 25 to 30° C. for yeast, and around 37° C. for eukaryotic cells. As for the culture conditions, reference can be made to Gene Expression Experiment Manual (Kodansha Ltd.) and the like.

As the host cell, there can be used *Rhizopus niveus*, *Rhizopus delemar* and higher eukaryotes (for example, CHO cells), in addition to bacteria such as *E. coli* and *Bacillus subtilis* and yeasts such as *Candida utilis*, *Saccaromyces cerevisiae* and *Pichia pastoris*. As *Bacillus subtilis*, a microorganism belonging to the genus *Bacillus* is preferably used. The genus *Bacillus* is known to include strains secreting a protein extracellularly (for example, *Bacillus subtilis*). Also, strains hardly secreting protease are known, and it is also preferred to use such a strain as the host. In the present invention, the host cell is preferably yeast, a filamentous fungus or a bacterium, more preferably a bacterium, especially preferably *E. coli* or *Bacillus subtilis*. As indicated in the Examples which will be given below, when this gene was expressed using *E. coli* BL21 and *Bacillus subtilis* ISW1214 as the host, the enzyme activity was found in the purified protein in the case of *E. coli* BL21 and in the culture supernatant in the case of *Bacillus subtilis* ISW1214.

The recombinant enzyme produced by the transformant can be isolated/purified by an appropriate combination of known separation methods and purification methods. These separation/purification methods include methods using a difference in solubility, such as salt precipitation and solvent precipitation; methods using a difference in molecular weight, such as dialysis, ultrafiltration, gel filtration and SDS-polyacryl electrophoresis; methods using a difference in electric charge such as ion exchange chromatography; methods using a difference in hydrophobicity, such as hydrophobic chromatography and reversed phase chromatography; and, further, methods using a difference in isoelectric point, such as isoelectric focusing; and, additionally, affinity chromatography. In addition to the production method described in the Examples, as for common separation/purification methods, reference can be made, for example, to Theory and Practice on Enzymes and Other Proteins (Nankodo Co., Ltd.).

EXAMPLES

Hereinafter, the present invention will be described in more detail by way of the following examples, but is not limited thereto. Unless otherwise noted herein, the units "%" and "part" are on a mass basis, and numerical ranges are indicated on the premise that their end points are included therein. Unless otherwise noted herein, operation procedures were carried out in accordance with the method described in Molecular Cloning: A Laboratory Manual (Sambrook, Maniatis et al., Cold Spring Harbour Laboratory Press (1989)).

Example 1: Preparation of Enzyme

1. Construction of Expression Plasmid

Through search for novel enzymes for various microorganisms, a hypothetical protein derived from *Thermoanaerobacter siderophilus* (Accession number: WP_006569624.1) was selected, and the function thereof was analyzed. The amino acid sequence (SEQ ID NO: 1) and base sequence (SEQ ID NO: 2) of this hypothetical protein are shown in FIG. 1A and FIGS. 1B to 1C, respectively. The base sequence of SEQ ID NO: 2 was subjected to codon correction in order to optimize it for expression in *E. coli*.

In order to express a protein consisting of an amino acid sequence (SEQ ID NO: 3) in which the $1^{st}$ to $752^{th}$ amino acids from the N terminal had been deleted in the amino acid sequence of SEQ ID NO: 1, an expression plasmid was constructed using a base sequence of SEQ ID NO: 4 according to the following procedures.

The target gene (base sequence of SEQ ID NO: 4) was PCR-amplified using a primer added with sequences of 15 bases homologous to both terminals of a vector pET32b (Novagen, Germany). The PCR conditions are indicated below. The total amount of a reaction solution for the PCR amplification was 50 µL.

| | |
|---|---|
| 5 × PS buffer (Takara Bio Inc.) | 10 µL |
| 2 mM dNTP mix (Takara Bio Inc.) | 2 µL |
| 20 µM primer (Ts_p20283242_R) | 1 µL |
| 20 µM primer (T_p32_d1-752S) | 1 µL |
| 100 ng/µL template | 1 µL |
| Primestar HS DNA Polymerase (Takara Bio Inc.) | 0.2 µL |
| H₂O | 34.8 µL |

The primers used are indicated in Table 1.

TABLE 1

| Primer | Sequence (5' → 3') |
|---|---|
| T_p32_d1-752S (Sense) | TTCTGGTCTGGTGCCACGCGGTTCTGGTCAATA TGAAGCGGAATA (SEQ ID NO: 5) |

TABLE 1-continued

| Primer | Sequence (5' → 3') |
|---|---|
| T_p32_d1-752R (Antisense) | CGAGTGCGGCCGCAAGCTTGTCGACTTAGAAAT CTGGCAAACGCG (SEQ ID NO: 6) |

A program for the PCR amplification reaction involved retaining the reaction solution at 96° C. for 1 minute, and then performing a cycle of 96° C. for 10 seconds→55° C. for 30 seconds→72° C. for 3 minutes 25 times. The resultant PCR product was subjected to agarose gel electrophoresis, and a band corresponding to the amplified fragment (2,418 bp) was cut from the gel, and extracted and purified using Wizard SV Gel and PCR Clean-Up System (Promega, Madison, Wis., USA).

In order to prepare a linearized plasmid used in an In-fusion (registered trademark) cloning reaction, pET32b was used as a template to perform PCR using primers indicated in Table 2.

TABLE 2

| Primer | Sequence (5' → 3') | Direction |
|---|---|---|
| pET32b_s | GTCGACAAGCTTGCGGCCGC (SEQ ID NO: 7) | Sense |
| pET32b_r | AGAACCGCGTGGCACCAGAC (SEQ ID NO: 8) | Antisense |

The composition of the reaction solution for the PCR amplification was identical with that of the reaction solution for the amplification of the target gene, except the primers used. A program for the PCR amplification reaction involved retaining the reaction solution at 96° C. for 1 minute, and then performing a cycle of 96° C. for 10 seconds→55° C. for 30 seconds→72° C. for 4 minutes 25 times. The amplified fragment was recovered by ethanol precipitation, and then treated with a restriction enzyme DpnI to digest the vector DNA. This product was subjected to agarose gel electrophoresis, and a band corresponding to the target DNA fragment (5,900 bp) was cut, and extracted and purified according to the same procedures as is the case with the target gene. The amplified target gene and vector pET32b were ligated using the In-Fusion HD Cloning Kit (Takara Bio Inc.). The ligation reaction was performed by retaining them at 50° C. for 20 minutes.

Mixed were 2.5 µL of the reaction solution containing the ligation reaction product and 50 µL of *E. coli* DH5α Competent Cells, and the solution was allowed to stand on ice for 1 hour, subjected to heat shock at 42° C. for 60 seconds, and then retained on ice for 3 minutes. To the mixture, 900 µL of an SOC medium (20 g/mL triptone, 5 mg/mL yeast extract, 8.6 mM NaCl, 2.5 mM KCl, 20 mM magnesium sulfate and 20 mM D-glucose) was added for shaking culture at 37° C. for 30 minutes. Bacterial cells were recovered by centrifugation (6,000×g, 4° C., 10 minutes), and cultured at 37° C. overnight in an LB agar medium containing 100 µg/mL ampicillin (10 mg/mL triptone, 5 mg/mL yeast extract, 1% NaCl and 1.5 w/v % agar). The resultant colonies were suspended in 2 mL of an LB liquid medium containing 100 µg/mL ampicillin (1% triptone, 0.5% yeast extract and 0.5% sodium chloride), and cultured with shaking overnight. A plasmid DNA was extracted from the resultant bacterial cells by the alkaline-SDS method (Birnboim and Doly, 1979). The resultant plasmid was defined as a mutant enzyme Δ (1-752)-*E. coli* expression plasmid.

2. Preparation of Recombinant Enzyme

The mutant enzyme Δ (1-752)-*E. coli* expression plasmid was introduced into *E. coli* BL 21 (DE: 3), inoculated into 30 mL of an LB medium containing 100 μg/mL ampicillin, and cultured with shaking at 37° C. overnight. This culture solution (30 mL) was subcultured in 1 L of the same medium, and cultured under the same conditions until the turbidity (600 nm) reached 0.5. Added was 0.1 M isopropyl β-D-1-thiogalactoside (IPTG) to attain a final concentration of 0.1 mM, and induction culture was started. After induction, shaking culture was performed at a culture temperature of 18° C. for 22 hours. Centrifugation (6,000×g, 4° C., 10 minutes) was performed to recover bacterial cells. The bacterial cells were suspended in a 10 mM sodium phosphate buffer (pH: 8.0), and crushed ultrasonically. Ultrasonication was performed three times for 1 minute each, under the conditions of duty cycle: 50% and output control: 3, using Sonifier 250 (Branson, Danbury, Conn.). Each ultrasonication was followed by 1-minute ice cooling. Centrifugation (12,000×g, 10 minutes, 4° C.) was performed twice, and the resultant extract liquid was used as a crude enzyme liquid. The crude enzyme liquid was obtained in an amount of 34 mL. $Ni^{+2}$ was chelated with 0.5 M $NiSO_4$ in advance, and the crude enzyme liquid was subjected to an Ni-chelating Sepharose Fast Flow column (1.0 i.d.×7 cm, 5.5 mL; GE Healthcare Bioscience, Uppsala, Sweden) equilibrated with a 10 mM sodium phosphate buffer (pH: 8.0) containing 0.5 M NaCl. A non-adsorbed protein was eluted with a 10 mM sodium phosphate buffer (pH: 8.0), and fractionated into 60 fractions in each amount of 15 mL. An adsorbed protein was eluted with an imidazole linear concentration gradient (30 to 500 mM, 400 mL), and fractionated into 80 fractions in each amount of 5 mL. Active fractions 88 to 101 were recovered. The recovered fractions were dialyzed, four times, against 1 L of a 10 mM sodium phosphate buffer (pH: 7.0). UC16-32-100 (Sanko Junyaku Co., Ltd., Tokyo) was used as a dialysis membrane. The sample after the dialysis was concentrated using Vivaspin 20 (MWCO: 30,000) (Sartorius, Goettingen, Germany). This product was a purified enzyme of the mutant enzyme Δ (1-752), which was stored at 4° C.

Example 2: Extracellular Expression Using *Bacillus subtilis* as Host

1. Construction of Expression Plasmid

An expression plasmid for producing the mutant enzyme Δ (1-752) by *Bacillus subtilis* was constructed. Firstly, the Δ (1-752)-*E. coli* expression plasmid constructed in Example 1 was used as a template to PCR-amplify the target gene using a primer added with base sequences homologous to the terminals of the vector for the sense chain amplification and a primer added with a part of the His-Tag sequence for the antisense chain amplification. The PCR conditions are indicated below. The total amount of a reaction solution for the PCR amplification was 50 μL.

| | |
|---|---|
| 5 × Primestar GXL buffer (Takara Bio Inc.) | 10 μL |
| 2.5 mM dNTPs mix (Takara Bio Inc.) | 4 μL |
| 10 μM primer (TSDD-F) | 1 μL |
| 10 μM primer (TSDD-R) | 1 μL |
| 1 ng/μL template | 1 μL |
| Primestar GXL DNA Polymerase (Takara Bio Inc.) | 1 μL |
| $H_2O$ | 32 μL |

The primers used are indicated in Table 3.

TABLE 3

| Primer | Sequence (5' → 3') |
|---|---|
| TSDD-F (Sense) | ACTGCTCTTGGATCCGGTCAATATGAAGCGGAATAC (SEQ ID NO: 9) |
| TSDD-R (Antisense) | ATGGTGATGGTGGTGGAAATCTGGCAAACGCG (SEQ ID NO: 10) |

A program for the PCR amplification reaction involved retaining the reaction solution at 96° C. for 1 minute, and then performing a cycle of 98° C. for 10 seconds→60° C. for 15 seconds→68° C. for 3 minutes 30 times. The resultant PCR product was subjected to agarose gel electrophoresis, and a band corresponding to the amplified fragment (2,451 bp) was cut from the gel, and extracted and purified using the Illustra™GFX™ PCR DNA and Gel Band Purification Kit (GE).

In order to prepare a linearized plasmid used in an In-fusion (registered trademark) cloning reaction, a plasmid obtained by modifying the vector pJEXOPT2 (see JP 2009-17841 A and JP 2009-17842 A) so as to optimize it for the present example was used as a template to perform PCR using primers indicated in Table 4. A primer added with His-Tag sequences at the terminals of the vector was used for the sense chain amplification, and a primer set so as to amplify the antisense chain from the terminals of the vector was used for the antisense chain amplification.

TABLE 4

| Primer | Sequence (5' → 3') |
|---|---|
| pJEXOPT2-F (Sense) | CACCACCATCACCATCATTGAGTCGACCTGCAGATC TCTAGA (SEQ ID NO: 11) |
| pJEXOPT2-R (Antisense) | GGATCCAAGAGCAGTGGC (SEQ ID NO: 12) |

The composition of the reaction solution for the PCR amplification was identical with that of the reaction solution for the amplification of the target gene, except the primers used. A program for the PCR amplification reaction involved retaining the reaction solution at 96° C. for 1 minute, and then performing a cycle of 98° C. for 10 seconds→60° C. for 15 seconds→68° C. for 7 minutes 30 times. The amplification product was subjected to agarose gel electrophoresis, and a band corresponding to the target DNA fragment (6,900 bp) was cut, and extracted and purified using Wizard SV Gel and PCR Clean-Up System. The amplified target gene and the amplified fragment of the vector pJEXOPT2 were ligated using the In-Fusion HD Cloning Kit (Takara Bio Inc.). The ligation reaction was performed by retaining them at 50° C. for 15 minutes.

The ligation reaction solution (2.5 μL) was used for transformation of *E. coli* DH5α, and a plasmid DNA was prepared from this culture solution using the Illustra™ plasmidPrep Mini Spin Kit (GE). The resultant plasmid was defined as a mutant enzyme Δ (1-752)-*Bacillus subtilis* expression plasmid.

2. Preparation of Recombinant Enzyme

Figure 3:
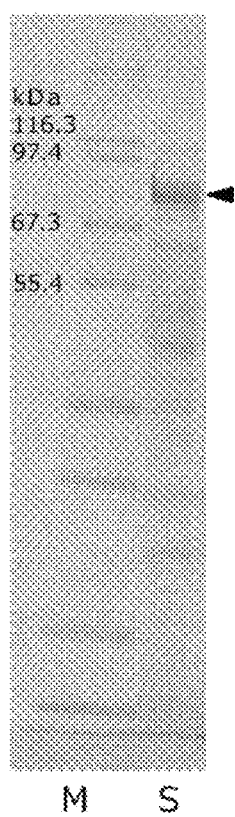
FIG. 3: SDS-PAGE of a mutant enzyme Δ (1-752) derived from *Thermoanaerobacter siderophilus*. M: molecular weight marker, and S: extracellular supernatant of *Bacillus subtilis*. The band of the mutant enzyme Δ (1-752) is shown by an arrow.

The mutant enzyme Δ (1-752)-*Bacillus subtilis* expression plasmid was introduced into *Bacillus subtilis* ISW1214 (Takara Bio Inc.) converted in the form of a protoplast, and cultured at 30° C. for 2 days in a regeneration agar medium containing 7.5 μg/mL tetracycline (composition: 8.1% sodium succinate, 1% agar, 0.5% casamino acid, 0.5% yeast extract, 0.15% potassium dihydrogen phosphate, 0.35% dipotassium hydrogen phosphate, 0.5% glucose, 0.4% magnesium chloride, 0.01% bovine serum albumin, 0.001% methionine, and 0.001% leucine). The resultant colonies were cultured in a pre-culture medium and, subsequently, a main culture medium (cultured in a manner as described in JP 2009-17841 A and JP 2009-17842 A, but the media used each had a modified composition). Centrifugation (15,000× g, 4° C., 5 minutes) was performed, and a solution obtained by filtering the supernatant through a 0.45-μm filter (Merk) was used as an enzyme solution of the mutant enzyme Δ (1-752). The enzyme solution was subjected to SDS-PAGE to confirm the production of a recombinant enzyme. A dark band was observed at 80 to 90 kDa close to a theoretical molecular weight size (about 91.5 kDa) of the mutant enzyme Δ (1-752), and it was confirmed that the mutant enzyme Δ (1-752) was secreted in the culture supernatant (FIG. 3).

Example 3: Activity Measurement

In order to measure the activity of the purified enzyme Δ (1-752) obtained in Example 1 (Present Enzyme 1), the maltose degradation activity was measured.

The maltose degradation activity was measured based on the amount of glucose produced. The amount of glucose was quantified by the glucose oxidase/peroxidase method (Miwa et al., 1972). For dilution of the enzyme, a 10 mM sodium acetate buffer (pH: 4.5) containing 1 mg/mL BSA was used. The composition of the enzyme reaction solution (total amount: 50 μL) is as follows.

| | |
|---|---|
| 100 mM sodium acetate buffer (pH 4.5) | 20 μL |
| 50 mM maltose | 20 μL |
| Purified enzyme Δ (1-752) solution | 10 μL |

The enzyme reaction solution was retained at 37° C. for 10 minutes to cause a reaction. After the elapse of 10 minutes of the reaction, the reaction was stopped by mixing 50 μL of the enzyme reaction solution and a 2M tris-hydrochloric acid buffer (pH: 7.0). To the enzyme reaction solution subjected to the reaction stopping treatment, 20 μL of a glucose quantification reagent (Wako Pure Chemical Industries, Ltd., Glucose C-II) was added, and the solution was retained at 37° C. for 30 minutes. Thereafter, the absorbance (wavelength: 505 nm) was measured with an ultraviolet visible spectrophotometer, JASCO V-630 BIO Spectrophotometer (JASCO Corporation, Tokyo). Based on a calibration curve prepared with D-glucose (NACALAI TESQUE, INC., Kyoto) having a concentration of 0 to 0.5 mM, the glucose concentration of the enzyme reaction solution was determined. The amount of enzyme producing 1 μmol glucose per minute, under the conditions of the present example, was defined as 1 U of the maltose degradation activity.

Example 4: Physicochemical Properties of Enzyme (pH and Temperature)

The physicochemical properties of the present enzyme were confirmed by measuring the maltose degradation activity. The enzyme used was the purified enzyme Δ (1-752) (Present Enzyme 1) obtained in Example 1.

1. Optimum pH

Figure 4:
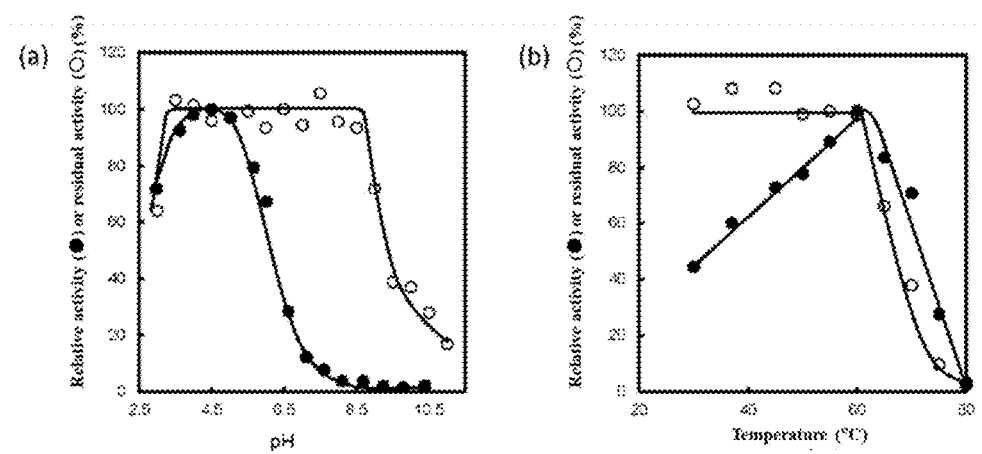
FIG. 4: Influence of the pH and temperature on the activity of the mutant enzyme Δ (1-752). (a) Black circles (●) each represent a relative activity (%) at each pH when the maximum enzyme activity is 100% (pH: 4.5), and white circles (○) each represent a residual activity (%) after retention at each pH (pH: 3.0 to 11.0) and 4° C. for 24 hours. (b) Black circles (●) each represent a relative activity (%) at each temperature when the maximum enzyme activity is 100% (temperature: 60° C.), and white circles (○) each represent a residual activity (%) after retention at each temperature for 15 minutes.

The maltose degradation activity of the preset enzyme was measured in a buffer having a pH of 3.0 to 11.0. The maltose degradation activity was measured in accordance with the method described in "Example 3: Activity measurement." However, a 40 mM Britton-Robinson (BR) buffer (pH: 3.0 to 11.0) was used as the reaction buffer. The present enzyme exhibited the maximum activity at a pH of 4.5, exhibited an activity of at least 90% relative to the maximum activity at a pH of 3.5, 4.0 and 5.0, and exhibited an activity of at least 98% relative thereto at a pH of 4.0 to 5.0 (FIG. 4a, black circles).

2. pH Stability

Mixed were 75 μL of a 0.1 M BR buffer at each pH (pH: 3.0 to 11.0) and 75 μL of 4.08 μg/mL the present enzyme to obtain a diluted enzyme solution, which was retained at 4° C. for 24 hours. The diluted enzyme solution after retention for 24 hours was used to measure the activity in accordance with the method described in "Example 3: Activity measurement." The proportion (%) of the activity after retention (residual activity), relative to the activity before retention in the 0.1 M BR buffer at each pH, was calculated. When the pH range in which the present enzyme exhibited a residual activity of 85% or more was determined as the stable pH range, the stable pH range was 3.5 to 8.5 (FIG. 4a, white circles).

3. Optimum Temperature

The enzyme reaction temperature was set to 30, 37, 45, 50, 55, 60, 65, 70, 75 or 80° C., and the maltose degradation activity was measured at each enzyme reaction temperature in accordance with the method described in "Example 3: Activity measurement." The present enzyme exhibited the maximum activity at a temperature of 60° C., and exhibited an activity of 80% or more relative to the maximum activity within a temperature range of 55 to 60° C. (FIG. 4b, black circles).

4. Temperature Stability

Mixed were 20 μL of a 0.1 M sodium acetate buffer (pH: 4.5) and 10 μL of 10.2 μg/mL the present enzyme, and the solution was retained at 30, 37, 45, 50, 55, 60, 65, 70, 75 or 80° C. for 15 minutes. The activity of the present enzyme after retention at each temperature was measured in accordance with the method described in "Example 3: Activity measurement." The proportion (%) of the activity after retention (residual activity), relative to the activity before retention at each temperature, was calculated. When the present enzyme exhibited a residual activity of 90% or more, it was determined to be stable at the temperature. The present enzyme was stable at a temperature of 60° C. or less (FIG. 4b, white circles).

Example 5: HPAEC-PAD Analysis of Enzyme Reaction Product

Reaction products of substrates by the mutant enzyme Δ (1-752) were analyzed by HPAEC-PAD (High performance anion-exchange chromatography with pulsed amperometric detection; anion chromatography with a pulsed amperometric detector). The substrates used were maltose (G2), maltotriose (G3), maltotetraose (G4), maltopentaose (G5), isomaltose (IG2), and isomaltotriose (IG3).

A reaction solution (1 mL) containing the enzyme Δ (1-752) (Present Enzyme 1) obtained in Example 1, 10 mM each substrate and a 42 mM sodium acetate buffer (pH: 4.5) was retained at 37° C. to cause a reaction. At 3, 6, 9 and 15 minutes after the beginning of the reaction, 180 μL was collected from the reaction solution. With the collected 180-μL reaction solution, 20 μL of 1 mM inositol (internal standard) was mixed. Then, the reaction solution was thermally treated at 100° C. for 3 minutes, and the reaction was stopped. For each substrate, four 200-μL reaction solutions reacted for 3 to 15 minutes were obtained. For dilution of the enzyme, a 10 mM sodium acetate buffer (pH: 4.5) containing 1 mg/mL BSA was used. The enzyme concentration used in the reaction varies depending on the substrate. The enzyme concentrations are indicated in Table 5.

TABLE 5

|  | Enzyme concentration | NaOH concentration of eluent |
| --- | --- | --- |
| Maltose | 5.41 nM | 400 mM |
| Maltotriose | 0.867 nM | 400 mM |
| Maltotetraose | 0.867 nM | 400 mM |
| Maltopentaose | 0.867 nM | 640 mM |
| Isomaltose | 43.3 nM | 160 mM |
| Isomaltotriose | 4.33 nM | 160 mM |

Each of the 200-μL reaction solutions was desalted with Amberlite MB4 (ORGANO CORPORATION, Tokyo), filtered using a 0.45-μm disposable membrane filter unit (Advantech Co., Ltd., Tokyo), and used as an analytical sample. The analytical sample (10 μL) was injected into a column. CarboPac PAI (0.4 cm i.d.×25 cm; Dionex) was used as the column. The NaOH concentrations of the respective eluents are indicated in Table 5. A saccharide analyzer (HPAEC-PAD, manufactured by Dionex) was used to determine the concentrations of the initial transfer products of the respective substrates. As the concentrations of the initial transfer products, for example, in the reaction using maltopentaose as the substrate, the maltohexaose concentration was calculated based on the standard curve (10 to 100 μM). Inositol (100 μM) was used as the internal standard and used for area correction.

Figure 5:
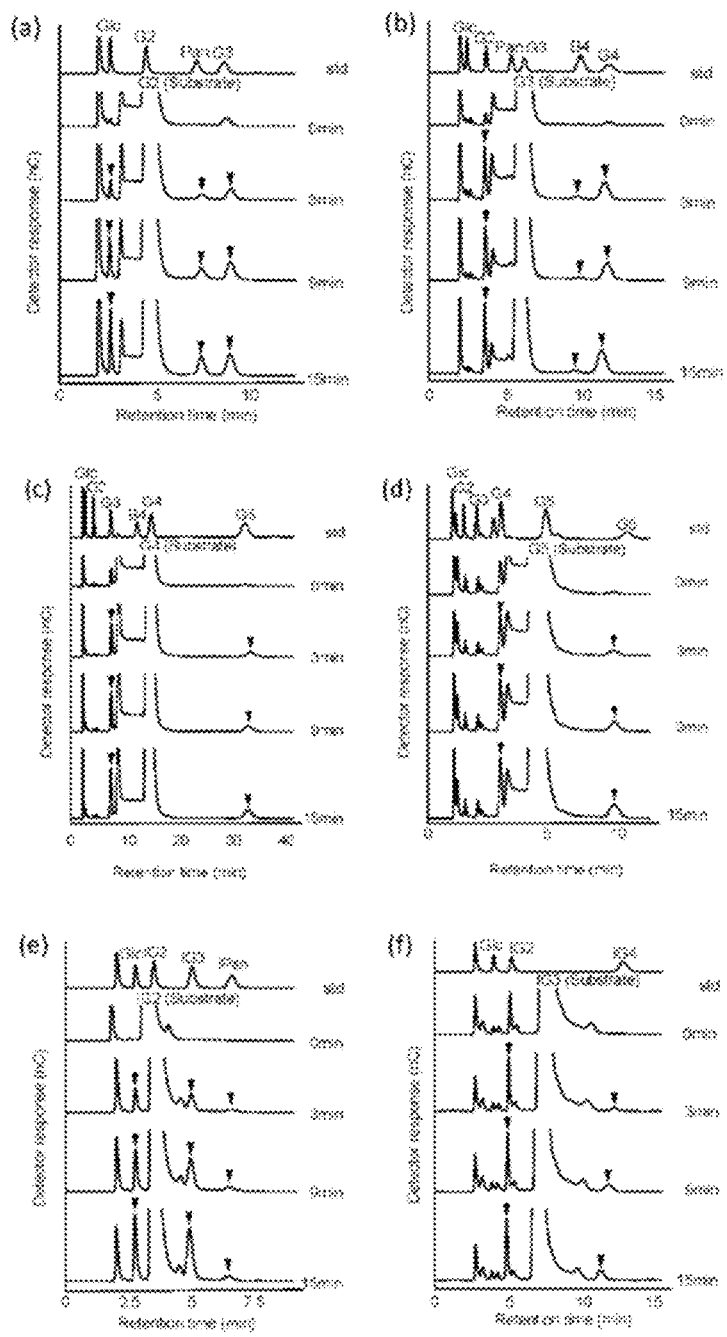
FIG. 5: HPAEC-PAD analysis of reaction products of the mutant enzyme Δ (1-752). The substrates are (a) maltose (G2), (b) maltotriose (G3), (c) maltotetraose (G4), (d) maltopentaose (G5), (e) isomaltose (IG2) and (f) isomaltotriose (IG3). For the respective substrates, chromatograms of a standard sample (std), a sample at 0 minute of the enzyme reaction time (0 min), a sample at 3 minutes (3 min), a sample at 9 minutes (9 min), and a sample at 15 minutes (15 min) are shown from the top. Glc: glucose, Pan: panose, B4: $6^3$-O-α-D-glucosylmaltotriose, IPan: isopanose, and G6: maltohexaose.

When maltose (G2) was used as the substrate, glucose (Glc), panose (Pan) and maltotriose (G3) were produced by the present enzyme (FIG. 5a). The velocity of panose production by the α-1,6 transfer reaction was 10.8 μmol/min/mg, and the velocity of maltotriose production by the α-1,4 transfer reaction was 4.39 μmol/min/mg. The α-1,6 transfer reaction velocity was 2.46 times faster than the α-1,4 transfer reaction velocity.

When maltotriose (G3) was used as the substrate, glucose (Glc), maltotetraose (G4) and $6^3$-O-α-D-glucosylmaltotriose (B4) were produced by the present enzyme (FIG. 5b). The velocity of maltotetraose production by the α-1,4 transfer reaction was 94.5 μmol/min/mg, and the velocity of $6^3$-O-α-D-glucosylmaltotriose production by the α-1,6 transfer reaction was 7.20 μmol/min/mg. The present enzyme was understood to mainly catalyze the α-1,4 transfer reaction with respect to the substrate maltotriose (G3). The α-1,4 transfer reaction velocity was 13.1 times faster than the α-1,6 transfer reaction velocity.

When maltotetraose (G4) was used as the substrate, maltotriose (G3) and maltopentaose (G5) were produced by the present enzyme (FIG. 5c). The α-1,4 transfer reaction velocity was 54.1 μmol/min/mg.

When maltopentaose (G5) was used as the substrate, maltotetraose (G4) and maltohexaose (G6) were produced by the present enzyme (FIG. 5d). The α-1,4 transfer reaction velocity was 81.7 μmol/min/mg.

When isomaltose (IG2) was used as the substrate, glucose (Glc), isomaltotriose (IG3) and isopanose (IPan) were produced by the present enzyme (FIG. 5e). The velocity of isomaltotriose production by the α-1,6 transfer reaction was 3.72 μmol/min/mg, and the velocity of isopanose production by the α-1,4 transfer reaction was 0.363 μmol/min/mg. The α-1,6 transfer reaction velocity was 10.2 times faster than the α-1,4 transfer reaction velocity.

When isomaltotriose (IG3) was used as the substrate, isomaltose (IG2) and isomaltotetraose (IG4) were produced by the present enzyme (FIG. 5f). The velocity of isomaltotetraose production by the α-1,6 transfer reaction was 11.1 μmol/min/mg.

Through the experiment in the reaction time of up to 15 minutes, it was demonstrated that the present enzyme mainly catalyzes the α-1,6 transfer reaction in some cases and mainly catalyzes the α-1,4 transfer reaction in the other cases, depending on the substrate used. For example, under the conditions of Example 5, the present enzyme was understood to mainly catalyze the α-1,4 transfer reaction when maltooligosaccharides G3, G4 and G5 were used as the substrates, but to catalyze the α-1,6 transfer reaction more than the α-1,4 transfer reaction when maltose (G2) and isomaltooligosaccharides were used as the substrate, in a short reaction time, i.e., around 15 minutes.

Example 6: Analysis of Change in Enzyme Reaction Over Time

Reaction products of substrates by the enzyme Δ (1-752) were analyzed over time by TLC (thin-layer chromatography).

Firstly, the enzyme Δ (1-752) (Present Enzyme 1) obtained in Example 1 was allowed to act on the substrate maltopentaose (G5). Specifically, 1 mL of a reaction solution having the following composition was retained at 37° C. to cause a reaction. For dilution of the enzyme, a 10 mM sodium acetate buffer (pH: 4.5) containing 1 mg/mL BSA was used.

Composition of Reaction Solution

| | |
| --- | --- |
| 30 mM Maltopentaose | 500 μL (final concentration: 15 mM) |
| Present enzyme solution | 400 μL (final concentration: 36.7 μg/mL) |
| 100 mM sodium acetate buffer (pH: 4.5) | 100 μL (final concentration: 10 mM) |

At 1, 6, 24, 48 and 96 hours after the beginning of the reaction, 100 μL was collected from the reaction solution and thermally treated at 100° C. for 3 minutes, and the reaction was stopped.

Next, an equal amount of *Rhizopus niveus*-derived glucoamylase (SEIKAGAKU CORPORATION) (5 U/mL, dissolved in a 0.1 M sodium acetate buffer (pH: 5.0)) was added to the reaction solutions reacted with the present enzyme for a period of 1 to 96 hours, and the reaction solutions were retained at 50° C. for 30 minutes.

Figure 6:
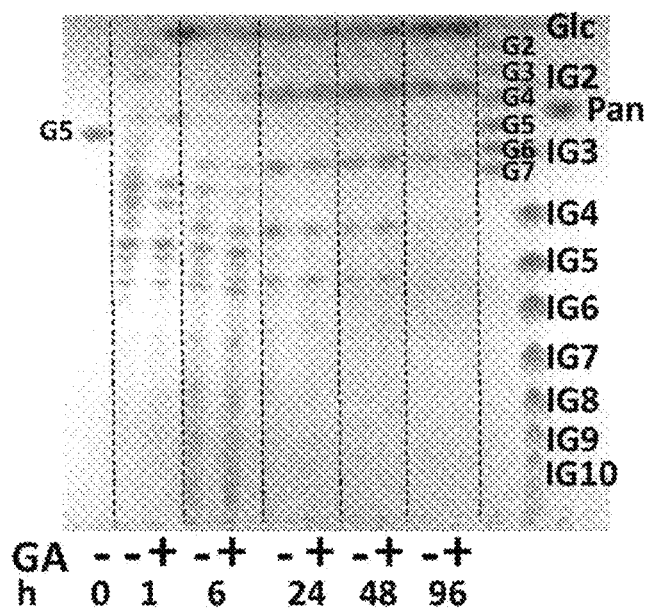
FIG. 6: TLC analysis of enzyme reaction products of the mutant enzyme Δ (1-752). The substrate is maltopentaose (G5). As for the "GA" indicated in the lower part of the sheet photograph, the symbol "−" represents samples not treated with glucoamylase, and the symbol "+" represents samples treated with glucoamylase. The figures of 0, 1, 6, 24, 48 and 96 for "h" each represent a reaction time of the mutant enzyme Δ (1-752) and the substrate.

The glucoamylase-treated reaction solutions and the untreated reaction solutions were analyzed by TLC. A Silica Gel 60F254 Aluminum Sheet (Merck, Darmstadt, Germany) was used as the TLC plate. As samples, 1 μL, of the respective reaction solutions were subjected to TLC. A development solvent composed of nitroethane:nitromethane:ethanol:water:1-propanol=1:1:3.5:4:5.5 (v/v/v/v/v) was used to perform development twice. After the development, the sheet was air-dried, and a detection liquid (acetic acid:sulfuric acid:anise aldehyde=100:2:1 (v/v/v) was sprayed. The sheet was heated to detect sugar. FIG. 6 is a photograph of the TLC sheet on which spots were detected.

In the TLC analysis, a plurality of spots of the maltooligosaccharides G2 to G7 degraded with glucoamylase were observed in the 1-hour reaction product by the present enzyme. Therefore, it is considered that the disproportionation reaction of maltooligosaccharides ($\alpha$-1,4-glucosyl transfer reaction) was catalyzed by the present enzyme (FIG. 6). Additionally, from the fact that a plurality of spots which were not degraded with glucoamylase were observed, it was confirmed that an $\alpha$-1,6 transfer product was also produced by the present enzyme.

The disappearance of spots due to glucoamylase degradation was not observed in the 6-hour reaction product by the present enzyme, and the production of maltooligosaccharides by the present enzyme was not detected. A reaction product having a degree of polymerization of around 10 was confirmed, but the production of a polymer which stayed at the spotted positions in the TLC sheet was not confirmed. This result is one of characteristics which demonstrate the difference of the present enzyme from *Gluconobacter oxydans*-derived dextrin dextranase.

The disappearance of spots due to glucoamylase degradation was not observed in the 24 to 96-hour reaction products by the present enzyme, and the production of maltooligosaccharides by the present enzyme was not detected. The spots which were not degraded with glucoamylase were observed at development positions equivalent to the marker sports of IG2 to IG5. However, as the reaction time was longer, long-chain products corresponding to IG3 to IG5 were degraded, so that the accumulation of glucose and the conversion into low-molecular isomaltooligosaccharides were found ($\alpha$-1,6-glucosidic bond hydrolysis activity).

Example 7: Saccharification Test 1

1. Method

Prepared were five reaction solutions each obtained by dissolving G67 rich syrup fraction-adjusted for this test in ultrapure water so as to attain a final concentration of 30%, and adding thereto a 1 M sodium acetate buffer (pH: 5.0) so as to attain a final concentration of 50 mM and $CaCl_2$) so as to attain a final concentration of 3 mM. A culture supernatant (Present Enzyme 2) of *Bacillus subtilis* containing the mutant enzyme $\Delta$ (1-752) prepared in Example 2 was added to each of the reaction solutions in an amount of 62.5, 125, 250, 500 or 1000 µL/g-DS to cause a reaction at 53° C. for 72 hours.

The sugar compositions of G67 rich syrup and the reaction products of the present enzyme were analyzed by HPLC. The analysis conditions were as follows: column: MCI GELCK02AS (Mitsubishi Chemical Corporation); eluent: ultrapure water; flow rate: 0.7 ml/min; column temperature: 80° C.; and detector: differential refractive index detector. The sugar composition (%) of each of the reaction products was calculated as an area ratio (%) of a peak corresponding to each saccharide when the total area of peaks detected by HPLC was 100. Since it had been revealed, from the peaks in the chromatographic data on starch hydrolysates, that the retention time of 30 minutes corresponds to DP30, an area ranging from the peak (retention time) of DP10 to the retention time of 30 minutes was calculated as an area of DP10 to 30.

In order to confirm the $\alpha$-1,6 bond production, the reaction products of the present enzyme were subjected to dextranase treatment. The dextranase treatment involved adding 20 µL of Dextranase L "Amano" diluted 200 times with a 200 mM sodium acetate buffer (pH: 5.0) to 0.5 mL of each of the samples having a solid content concentration of 1%, and retaining the mixture at 53° C. for 24 hours. After the dextranase treatment, the sugar composition was analyzed. The sugar compositions of the reaction products of the present enzyme and the sugar compositions thereof after the dextranase treatment were compared to calculate the increase proportions of DP1 to 3 after the dextranase treatment. The sugar compositions of DP1 to 3 were analyzed under the conditions: column Aminex HPX-42A (BioRad); eluent: ultrapure water; flow rate: 0.5 ml/min; column temperature: 75° C.; and detector: differential refractive index detector.

2. Results

FIGS. 7A, 7B, 7C-1 and 7C-2 show chromatograms of the HPLC analysis of G67 rich syrup and the reaction products by the present enzyme. Table 6 indicates the sugar compositions of G67 rich syrup and the reaction products of the present enzyme, and the increase proportions (%) of DP1 to 3 of the reaction products after the dextranase treatment.

TABLE 6

|  |  | G67 rich syrup | Reaction Product 7-1 | Reaction Product 7-2 | Reaction Product 7-3 | Reaction Product 7-4 | Reaction Product 7-5 |
|---|---|---|---|---|---|---|---|
| Amount (µL/g-DS) of enzyme $\Delta$ (1-752) added | | — | 62.5 | 125 | 250 | 500 | 1000 |
| Sugar composition (%) of reaction product | DP: ≥31 | 0 | 2.5 | 1.2 | 0.8 | 1 | 0.7 |
| | DP: 10-30 | 4.7 | 37.2 | 46.4 | 49.1 | 47.5 | 46.2 |
| | DP: 3-9 | 95.2 | 55.1 | 45.5 | 41.2 | 40.9 | 42 |
| | DP: 1-2 | 0.1 | 5.1 | 6.8 | 8.6 | 10.2 | 10.4 |
| Increase proportion (%) of DP: 1-3 after dextranase treatment | | — | +31 | +33 | +34.6 | +35.6 | +35.3 |

Figure 7A:
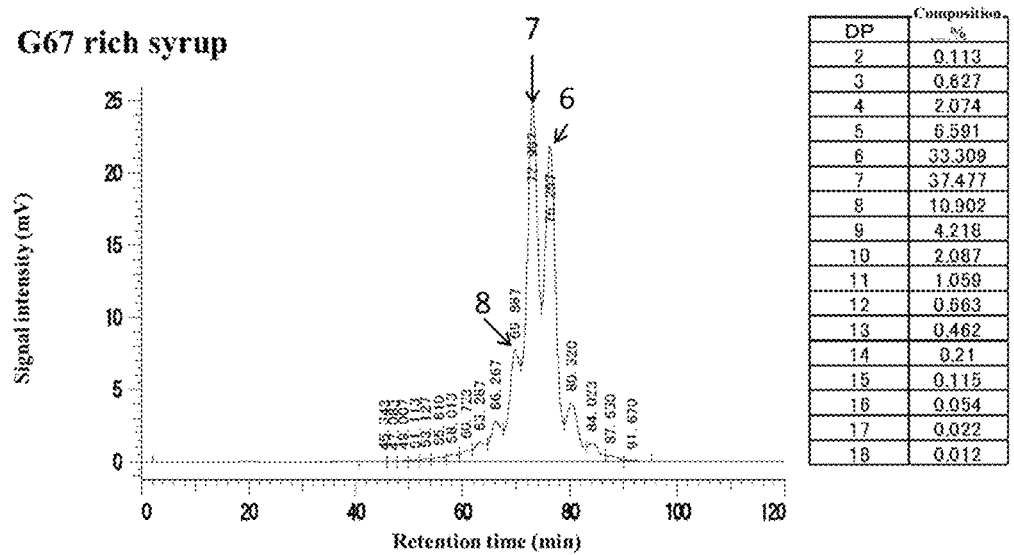
FIG. 7A: A chromatogram of HPLC analysis of the raw material G67 rich syrup. The figures of 6 to 8 given in the chromatogram indicate that the peaks to which the figures are added are corresponding to saccharides having a degree of polymerization of 6 to 8.
Figure 7B:
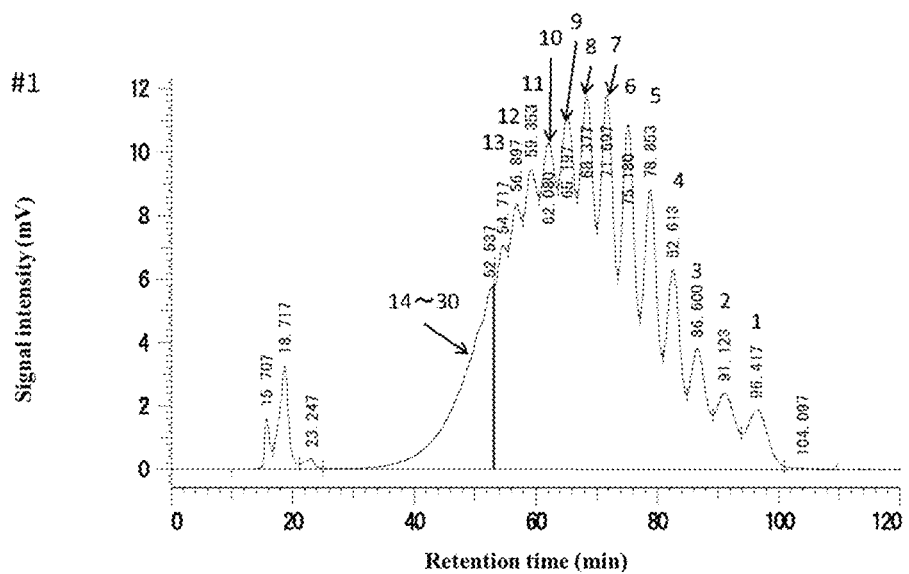
FIG. 7B: HPLC analysis of a reaction product prepared using G67 rich syrup as a raw material. This chromatogram is of Reaction Product 7-1 (#1). The figures of 1 to 13 given in the chromatogram indicate that the peaks to which the figures are added are corresponding to saccharides having a degree of polymerization of 1 to 13. Since it had been revealed, from the peaks in the chromatographic data on starch hydrolysates, that saccharides having a degree of polymerization of 30 are detected at about 30 minutes of the retention time, an area ranging from the peak corresponding to saccharides having a degree of polymerization of 14 (retention time: 52.537 minutes) to 30 minutes of the retention time was regarded as corresponding to saccharides having a degree of polymerization of "14 to 30."

The raw material G67 rich syrup contained saccharides of DP6 and DP7 in proportions of about 33% and about 37%, respectively, and contained saccharides of DP3 to 9 in a proportion of about 95% (FIG. 7A).

The content proportion of DP10 to 30 in the reaction products remarkably increase as compared with that in the raw material. The content proportion of DP10 to 30 is 4.7% in the raw material, but increases to 37.2% in Reaction Product 7-1 and is 46% or more in Reaction Products 7-2 to 7-5 (Table 6).

HPLC. The HPLC analysis and dextranase treatment were performed under the same conditions as in Example 7.

2. Results

FIGS. 8A, 8B, 8C-1 and 8C-2 show chromatograms of the HPLC analysis of Pinedex #1 and the reaction products by the present enzyme. Table 7 indicates the sugar compositions of Pinedex #1 and the reaction products of the present enzyme, and the increase proportions (%) of DP1 to 3 of the reaction products after the dextranase treatment.

TABLE 7

|  |  | Pinedex #1 | Reaction Product 8-1 | Reaction Product 8-2 | Reaction Product 8-3 | Reaction Product 8-4 | Reaction Product 8-5 | Reaction Product 8-6 |
| --- | --- | --- | --- | --- | --- | --- | --- | --- |
| Enzyme composition | Amount (μL/g-DS) of enzyme Δ (1-752) added | — | 125 | 125 | 125 | 625 | 625 | 625 |
|  | Kleistase L-1 (mg/g-DS) | — | 0.000 | 0.010 | 0.020 | 0.000 | 0.010 | 0.020 |
|  | GODO-FIA (U/g-DS) | — | 200 | 200 | 200 | 200 | 200 | 200 |
|  | Pullulanase "Amano" 3 (mg/g-DS) | — | 0.2 | 0.2 | 0.2 | 0.2 | 0.2 | 0.2 |
| Sugar composition (%) of reaction product | DP: ≥31 | 59.242 | 9.7 | 3.4 | 2.8 | 5.7 | 4.8 | 4.7 |
|  | DP: 10-30 | 16.991 | 59.7 | 57.6 | 55.8 | 52.2 | 51.9 | 51.4 |
|  | DP: 3-9 | 22.049 | 26.1 | 32.5 | 34.9 | 33.5 | 34 | 34.7 |
|  | DP: 1-2 | 1.717 | 4.3 | 6.2 | 6.3 | 8.2 | 8.8 | 8.8 |
| Increase proportion (%) of DP: 1-3 after dextranase treatment |  | — | +35.9 | +38.6 | +41.5 | +39.4 | +40.2 | +39.8 |

Figures 1, 7C:
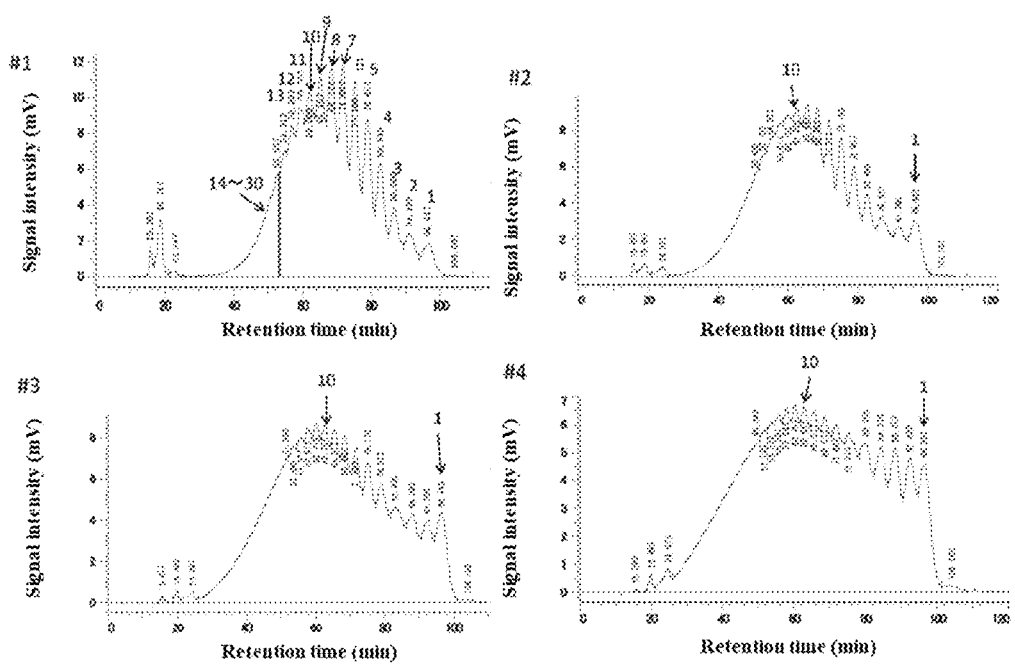
FIG. 7C: HPLC analysis of reaction products prepared using G67 rich syrup as a raw material. These chromatograms are of Reaction Products 7-1 (#1) to 7-5 (#5). The concentrations of enzyme added are (#1) 62.5, (#2) 125, (#3) 250, (#4) 500, and (#5) 1000 μL/g-DS. The chromatogram of #1 is identical with that in FIG. 7B. Also in the chromatograms of #2 to #5, peaks corresponding to saccharides having degrees of polymerization of 1, 2, 3, etc. are shown, in order, from the peak at the right end. Especially, the figures of 1 and 10 are added to the peaks corresponding to saccharides having degrees of polymerization of 1 and 10 to indicate the degrees of polymerization.
Figures 2, 7C:
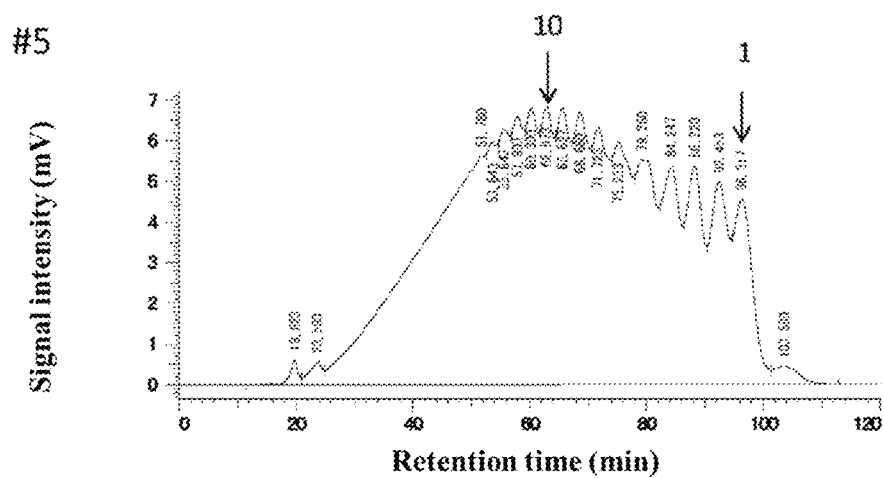

Also, there was a tendency that, as the amount of the present enzyme added increases, the content proportion of DP1 to 2 in the reaction products also increases (Table 6, and FIGS. 7C-1 and 7C-2).

On the other hand, the content proportion of DP 3 to 9 in the reaction products remarkably decreased as compared with that in the raw material. The content proportion of DP 3 to 9 is 95.2% in the raw material, but decreases to less than 40.9% in Reaction Product 7-4 having the lowest content proportion (Table 6).

For all of Reaction Products 7-1 to 7-5, the content proportion of DP 1 to 3 in the sample after the dextranase treatment was +30% or more relative to the content proportion of DP 1 to 3 in the reaction product before the treatment (Table 6). Since the increment of the content proportion of DP 1 to 3 was caused by hydrolysis of α-1,6 bonds with dextranase, it was confirmed that DP10 to 30 having increased in the reaction products were produced due to the α-1,6 transfer activity of the preset enzyme.

Example 8: Saccharification Test 2

1. Method

Prepared were six reaction solutions each obtained by dissolving Pinedex #1 (Matsutani Chemical Industry Co., Ltd.) in ultrapure water so as to attain a final concentration of 30%, and adding thereto a 1 M sodium acetate buffer (pH: 5.0) so as to attain a final concentration of 50 mM and CaCl$_2$) so as to attain a final concentration of 3 mM. A culture supernatant (Present Enzyme 2) of *Bacillus subtilis* containing the mutant enzyme Δ (1-752) prepared in Example 2, GODO-FIA (GODO SHUSEI CO., LTD.; isoamylase), Pullulanase "Amano" 3 (Amano Enzyme Inc.) and Kleistase L-1 (Amano Enzyme Inc.) were added to each reaction solution under the conditions indicated in Table 7 to cause a reaction at 53° C. for 72 hours. The sugar composition of each of the reaction products was analyzed by HPLC.

Figure 8A:
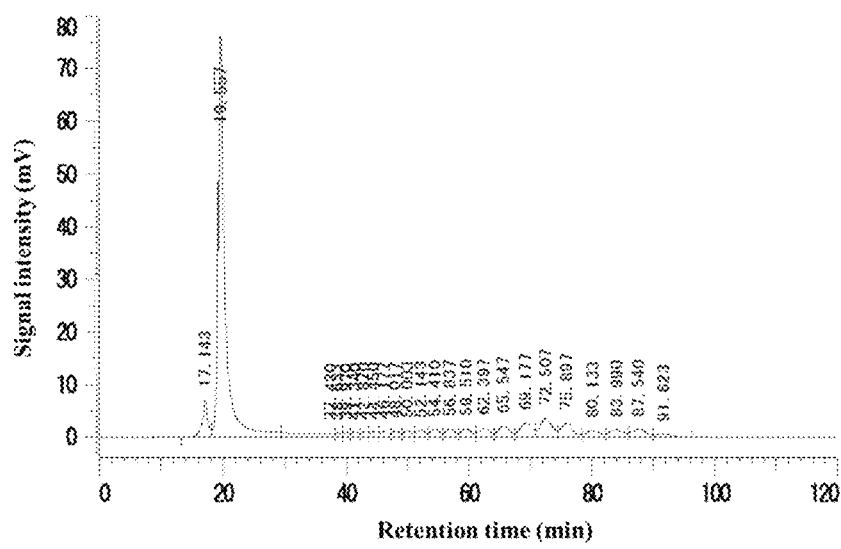
FIG. 8A: A chromatogram of HPLC analysis of Pinedex #1.
Figure 8B:
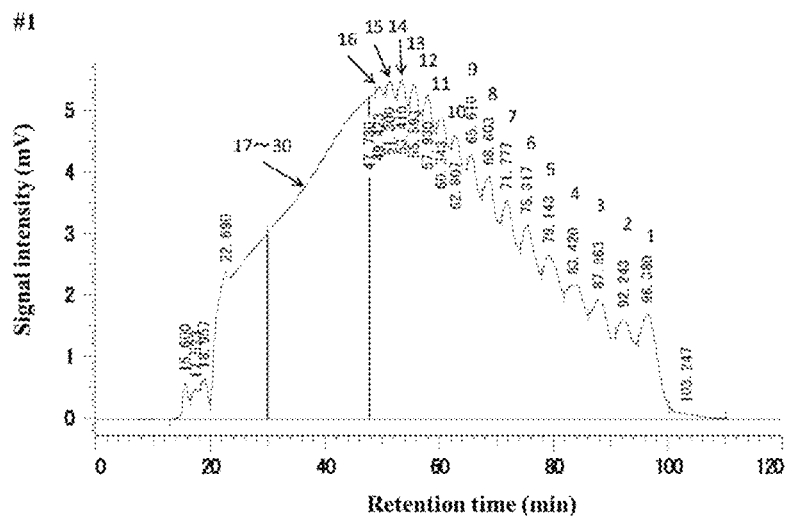
FIG. 8B: HPLC analysis of a reaction product prepared using Pinedex #1 as a raw material. This chromatogram is of Reaction Product 8-1 (#1). The figures of 1 to 16 given in the chromatogram indicate that the peaks to which the figures are added are corresponding to saccharides having degrees of polymerization of 1 to 16. Since it had been revealed, from the peaks in the chromatographic data on starch hydrolysates, that saccharides having a degree of polymerization of 30 are detected at about 30 minutes of the retention time, an area ranging from the peak corresponding to saccharides having a degree of polymerization of 17 (retention time: 47.730 minutes) to 30 minutes of the retention time was regarded as corresponding to saccharides having a degree of polymerization of "17 to 30."
Figures 1, 8C:
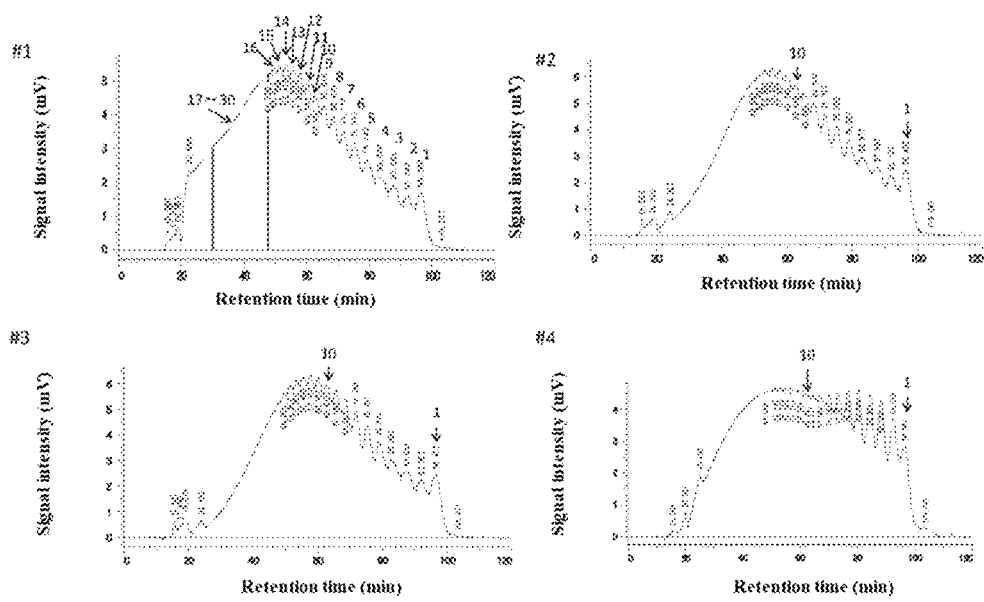
FIG. 8C: HPLC analysis of reaction products prepared using Pinedex #1 as a raw material. These chromatograms are of Reaction Products 8-1 (#1) to 8-6 (#6). The compositions of enzymes added are shown in Table 7. The chromatogram of #1 is identical with that in FIG. 8B. Also in the chromatograms of #2 to #6, peaks corresponding to saccharides having degrees of polymerization of 1, 2, 3, etc. are shown, in order, from the peak at the right end. Especially, the figures of 1 and 10 are added to the peaks corresponding to saccharides having degrees of polymerization of 1 and 10 to indicate the degrees of polymerization.
Figures 2, 8C:
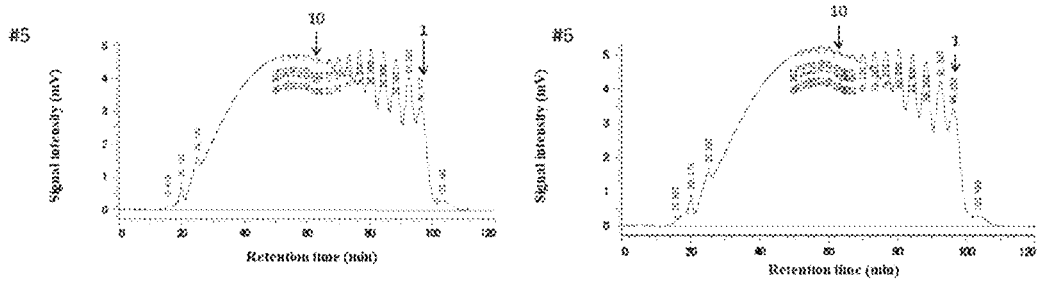

The raw material Pinedex #1 contained saccharides of DP31 or more in a proportion of about 60% (FIG. 8A).

The content proportion of DP10 to 30 in the reaction products remarkably increased as compared with that in the raw material. The content proportion of DP10 to 30 is 17% in the raw material, but increases to 50% or more in all the reaction products (Table 7). There was a tendency that the content proportions of DP 1 to 2 and DP 3 to 9 in the reaction products also increase as compared with those in the raw material. Also, there was a tendency that, as the amount of the present enzyme added increases, the content proportion of DP 1 to 2 in the reaction products increases, as is the case with Example 7.

On the other hand, the content proportion of DP 31 or more in the reaction products remarkably decreased as compared with that in the raw material. The content proportion of DP 31 or more is about 60% in the raw material, but decreases to less than 10% in all the reaction products (Table 7). The reduction in content proportion of the saccharides (dextrins) of DP 31 or more contained in the raw material Pinedex #1 is considered to have been caused by the action of the hydrolases (GODO-FIA, Pullulanase "Amano" 3 and Kleistase L-1).

Figures 1, 8D:
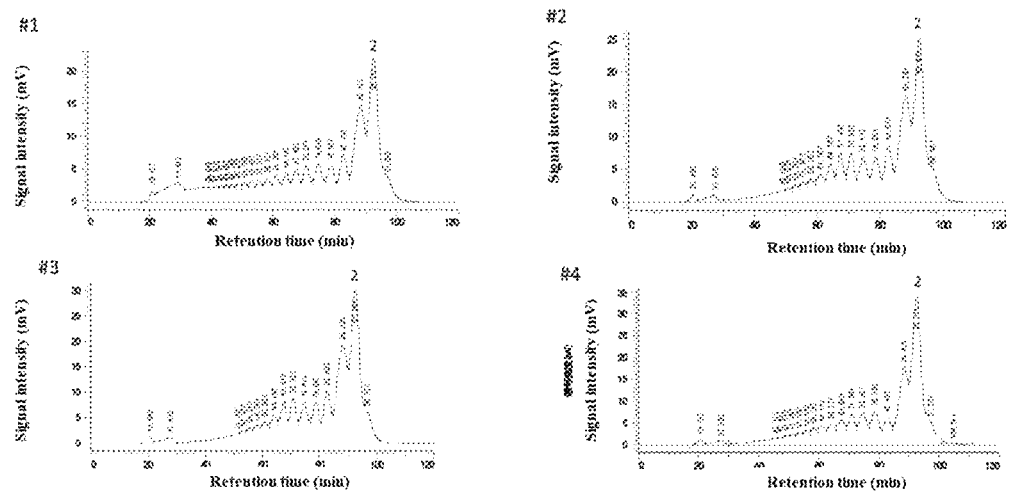
FIG. 8D: HPLC analysis of the reaction products prepared using Pinedex #1 as a raw material after dextranase treatment. These chromatograms are of Samples #1 to #6 after dextranase treatment. In all the chromatograms, the peak corresponding to saccharides having a degree of polymerization of 1 is unclear, and peaks corresponding to saccharides having degrees of polymerization of 2, 3, 4, etc. are shown, in order, from the highest peak at the right end. Especially, the figure of 2 is added to the peak corresponding to saccharides having a degree of polymerization of 2 to indicate the degree of polymerization.
Figures 2, 8D:
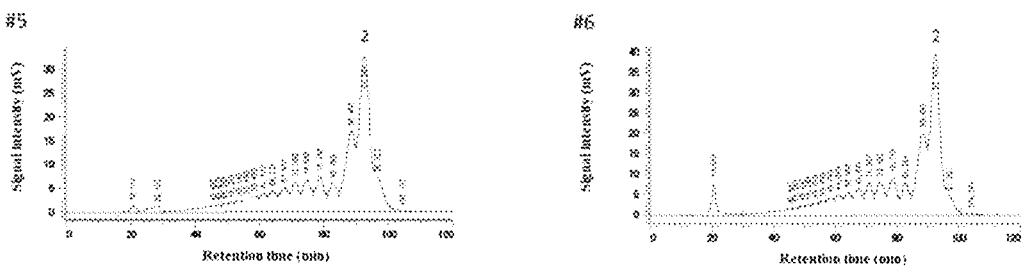

For all of Reaction Products 8-1 to 8-6, the content proportion of DP 1 to 3 in the sample after the dextranase treatment increased to 35% or more relative to the content proportion of DP 1 to 3 in the reaction product before the treatment (Table 7). The chromatograms of the samples after the dextranase treatment show lower peaks of DP4 or more, as shown in FIGS. 8D-1 and 8D-2. These facts demonstrate that the reaction products before the treatment were glucans having an α-1,6 bond.

INDUSTRIAL APPLICABILITY

The present invention is useful in various fields including food products and medicine in which α-1,6-glucan can be used.

SEQUENCE LISTING FREE TEXT

SEQ ID NO: 1. Amino acid sequence of hypothetical protein derived from *Thermoanaerobacter siderophilus*

SEQ ID NO: 2: Base sequence encoding hypothetical protein derived from *Thermoanaerobacter siderophilus*

SEQ ID NO: 3 Amino acid sequence of mutant enzyme Δ (1-752)

SEQ ID NO: 4: Base sequence encoding mutant enzyme Δ (1-752)

SEQ ID NOs: 5 and 6: Primers indicated in Table 1

SEQ ID NOs: 7 and 8: Primers indicated in Table 2

SEQ ID NOs: 9 and 10: Primers indicated in Table 3

SEQ ID NO: 11 and 12: Primers indicated in Table 4

---

The invention claimed is:

1. An enzyme having α-1,6-glucosyl transfer activity, which is any one of proteins (a), (b) and (c):
   (a) a protein consisting of the amino acid sequence of SEQ ID NO: 3;
   (b) a protein consisting of an amino acid sequence having at least 90% amino acid sequence identity to the amino acid sequence of SEQ ID NO: 3; and
   (c) a protein consisting of an amino acid sequence in which one or several amino acid(s) have been substituted, inserted, deleted or added in the amino acid sequence of SEQ ID NO: 3.

2. The enzyme according to claim 1, which further has α-1,4-glucosyl transfer activity.

3. An enzyme preparation for manufacturing α-1,6-glucan from an oligosaccharide or a polysaccharide having an α-1,4-glucosidic bond and/or an α-1,6-glucosidic bond, which comprises the enzyme according to claim 1.

4. The enzyme preparation according to claim 3, wherein the oligosaccharide or the polysaccharide having the α-1,4-glucosidic bond and/or the α-1,6-glucosidic bond are/is partially degraded starch product(s).

5. The enzyme preparation according to claim 3, wherein the α-1,6-glucan is an isomaltooligosaccharide or an isomaltomegalosaccharide having a degree of polymerization of 2 to 30.

6. A composition for catalyzing an α-1,6-glucosyl transfer reaction, comprising any one of proteins (a), (b), and (c):
   (a) a protein consisting of the amino acid sequence of SEQ ID NO: 3;
   (b) a protein consisting of an amino acid sequence having at least 90% amino acid sequence identity to the amino acid sequence of SEQ ID NO: 3; and
   (c) a protein consisting of an amino acid sequence in which one or several amino acid(s) have been substituted, inserted, deleted or added in the amino acid sequence of SEQ ID NO: 3.

7. The composition according to claim 6, which is used for manufacturing α-1,6-glucan from an oligosaccharide and/or a polysaccharide having an α-1,4-glucosidic bond or an α-1,6-glucosidic bond.

8. A method for manufacturing α-1,6-glucan, comprising a reaction step of allowing the enzyme according to claim 1 to act on an oligosaccharide or a polysaccharide having an α-1,4-glucosidic bond and/or an α-1,6-glucosidic bond to obtain α-1,6-glucan.

9. The method according to claim 8, which further comprises, before said reaction step, the step of hydrolyzing starch to obtain the oligosaccharide or the polysaccharide having the α-1,4-glucosidic bond and/or the α-1,6-glucosidic bond.

10. The method according to claim 8, further comprising preparing a food product, a feed, a bait, a cosmetic product, or a pharmaceutical product using the α-1,6-glucan.

11. A method for manufacturing a glycoside, comprising the step of allowing the enzyme according to claim 1 to act on a sugar acceptor and a sugar donor.

12. The method for manufacturing a glycoside according to claim 11, wherein the sugar donor is a maltooligosaccharide.

13. The method for manufacturing a glycoside according to claim 11, wherein the sugar acceptor is a compound having an alcoholic hydroxyl group or a compound having a phenolic hydroxyl group.

14. The method of claim 11, further comprising preparing a food product, a feed, a bait, a cosmetic product, or a pharmaceutical product using the glycoside.

15. A method for manufacturing α-1,6-glucan, comprising a reaction step of allowing the composition according to claim 6 to act on an oligosaccharide and/or a polysaccharide having an α-1,4-glucosidic bond or an α-1,6-glucosidic bond to obtain α-1,6-glucan.

\* \* \* \* \*